United States Patent
Reiffenrath et al.

[11] Patent Number: 5,487,845
[45] Date of Patent: * Jan. 30, 1996

[54] FLUOROBENZENE DERIVATIVES AND LIQUID-CRYSTALLINE MEDIUM

[75] Inventors: Volker Reiffenrath, Rossdorf; Hans A. Kurmeier, Seeheim-Jugenheim; Eike Poetsch, Mühltal; Herbert Plach, Darmstadt; Ulrich Finkenzeller, Plankstadt; Ekkehard Bartmann, Erzhausen; Joachim Krause, Dieburg; Bernhard Scheuble, Seeheim-Jugenheim, all of Germany

[73] Assignee: Merck Patent Gesellschaft Mit Beschrankter Haftung, Darmstadt, Germany

[ * ] Notice: The portion of the term of this patent subsequent to Oct. 10, 2012, has been disclaimed.

[21] Appl. No.: 229,842

[22] PCT Filed: Sep. 3, 1990

[86] PCT No.: PCT/EP90/01471

§ 371 Date: Nov. 19, 1990

§ 102(e) Date: Nov. 19, 1990

[87] PCT Pub. No.: WO91/03449

PCT Pub. Date: Mar. 21, 1991

Related U.S. Application Data

[63] Continuation of Ser. No. 623,385, Nov. 19, 1990, abandoned.

[30] Foreign Application Priority Data

Sep. 6, 1989 [DE] Germany .................... 39 29 525.7
Sep. 6, 1989 [DE] Germany .................... 39 29 526.5
Sep. 7, 1989 [DE] Germany .................... 39 29 764.0
Mar. 28, 1990 [DE] Germany .................... 40 09 907.5

[51] Int. Cl.$^6$ .................... C09K 19/30; C09K 19/12
[52] U.S. Cl. .................... 252/299.63; 252/299.66
[58] Field of Search .................... 252/299.63, 299.66

[56] References Cited

U.S. PATENT DOCUMENTS

| | | | |
|---|---|---|---|
| 4,393,231 | 7/1983 | Misaki et al. | 560/73 |
| 4,512,636 | 4/1985 | Andrews et al. | 359/104 X |
| 4,630,897 | 12/1986 | Andrews et al. | 359/104 X |
| 4,871,470 | 10/1989 | Wachtler et al. | 252/299.63 |
| 5,032,313 | 7/1991 | Goto et al. | 252/299.63 |
| 5,230,829 | 7/1993 | Bartmann et al. | 252/299.63 |
| 5,286,411 | 2/1994 | Rieger et al. | 252/299.63 |
| 5,308,541 | 5/1994 | Hittich et al. | 252/299.63 |
| 5,308,542 | 5/1994 | Poetsch et al. | 252/299.63 |
| 5,308,543 | 5/1994 | Sasaki et al. | 252/299.63 |

FOREIGN PATENT DOCUMENTS

| | | |
|---|---|---|
| 0387032 | 9/1990 | European Pat. Off. . |
| 0157523 | 12/1980 | Japan . |
| 0018326 | 2/1983 | Japan . |
| 0193191 | 9/1986 | Japan . |
| 2162515 | 2/1986 | United Kingdom . |
| 8808441 | 11/1988 | WIPO . |

*Primary Examiner*—Gary L. Geist
*Assistant Examiner*—C. Harris
*Attorney, Agent, or Firm*—Millen, White, Zelano, & Branigan

[57] ABSTRACT

Fluorobenzene derivatives of the formula I,

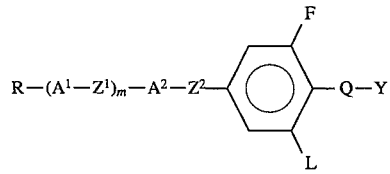

R, A1, A2, S1, 22, L, m, Y, Q are as defined herein.

36 Claims, No Drawings

FLUOROBENZENE DERIVATIVES AND LIQUID-CRYSTALLINE MEDIUM

This application is a continuation of application Ser. No. 07/623,385, filed Nov. 19, 1990 abandoned, which is based on international application PCT/EP90/01471, filed Sep. 3, 1990.

The invention relates to new fluorobenzene derivatives of the formula I

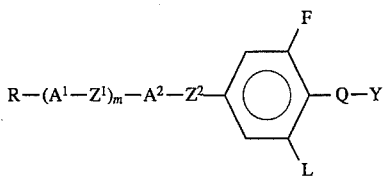

in which
R is H, an alkyl or alkenyl radical of 1 to 15 carbon atoms which is unsubstituted or monosubstituted by CN or $CF_3$ or at least monosubstituted by halogen, it being possible for one or more $CH_2$ groups in these radicals also to be replaced, in each case independently of one another, by

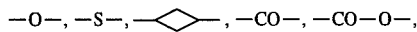

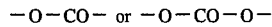

in such a manner that O atoms are not linked directly to one another,
$A^1$ and $A^2$, in each case independently of one another, are a
(a) trans-1,4-cyclohexylene radical, in which one or more non-adjacent $CH_2$ groups can also be replaced by —O— and/or —S—,
(b) 1,4-phenylene radical, in which one or two CH groups can also be replaced by N,
(c) radical from the group comprising 1,4-cyclohexenylene, 1,4-bicyclo[2.2.2]octylene, piperidine- 1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by CN or fluorine,
$Z^1$ and $Z^2$, in each case independently of one another, are —CO—O—, —O—CO—, —$CH_2$O—, —O$CH_2$—, —$CH_2CH_2$—, —CH=CH—, —C≡C— or a single bond, one of the radicals $Z^1$ and $Z^2$ is also —$(CH_2)_4$— or —CH=CH—$CH_2CH_2$—,
L is H or F,
m is 0, 1 or 2,
Y is F or Cl, and
Q is a single bond, —$CF_2$—, —$OCF_2$— or —OCHF—, with the proviso that L is F, if Q is a single bond.

The invention furthermore relates to the use of these compounds as components of liquid-crystalline media and to liquid-crystal and electrooptical display elements containing the liquid-crystalline media according to the invention.

The compounds of the formula I can be used as components of liquid-crystalline media, in particular for displays based on the principle of the twisted cell, the guest-host effect, the effect of the deformation of aligned phases or the effect of dynamic scattering.

The object of the invention was to find new stable liquid-crystalline or mesogenic compounds which are suitable as components of liquid-crystalline media and in particular have simultaneously a comparatively low viscosity and a relatively high dielectric anisotropy.

It has now been found that compounds of the formula I are highly suitable as components of liquid-crystalline media. In particular, they have comparatively low viscosities. By means of them, it is possible to obtain stable liquid-crystalline media having a road mesophase range and advantageous values for optical and dielectric anisotropy. These media furthermore have a very good low-temperature behaviour.

Liquid crystals of the formula

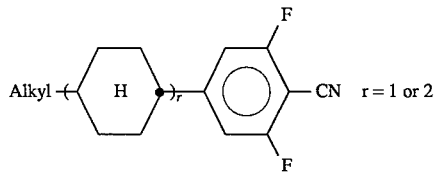

have already been disclosed in DE 3,209,179. Compounds of the formulae

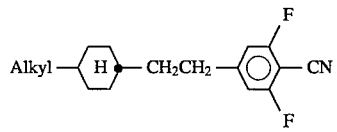

and

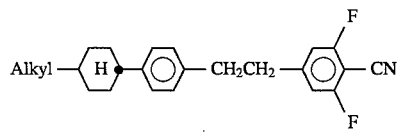

are disclosed in JP 62/103,057. Finally, compounds of the formula

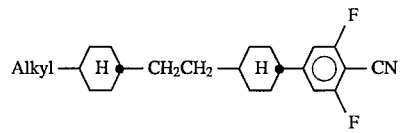

are described in JP 63,216,858. Compounds of the following formulae:

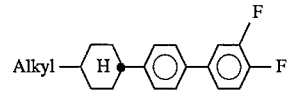

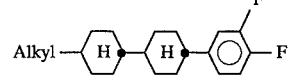

are disclosed in German Offenlegungsschriften 3,042,391 and 3,139,130.

Various compounds having liquid-crystalline properties and a terminally-bound $CF_3$ group are already known (U.S. Pat. No. 4,330,426; U.S. Pat. No. 4,684,476; J. C. Liang and S. Kumar, Mol. Cryst. Liq. Cryst. 1987; Vol. 142, pp. 77–84). However, these compounds often have a strongly smectogenic character and are less suitable for many practical applications.

However, in view of the wide range of applications of these compounds having a high Δε, it was desirable to have available further compounds of exactly tailor-made properties for the particular applications.

In addition, by providing the compounds of the formula I, the range of liquid-crystalline substances, which in the various aspects of industrial application are suitable for the preparation of liquid-crystalline mixtures, is very generally and significantly broadened.

The compounds of the formula I have a broad range of applications. Depending on the choice of substituents, these compounds can serve as base materials of which liquid-crystalline media are composed for the most part; however, it is also possible to add compounds of the formula I to liquid-crystalline base materials from other classes of compounds, in order, for example, to influence the dielectric and/or optical anisotropy of such a dielectric and/or to optimize its threshold voltage and/or its viscosity.

In the pure state, the compounds of the formula I are colorless and form liquid-crystalline mesophases in a temperature range favored for electrooptical use. They have very good chemical, heat and light stability.

Accordingly, the invention relates to compounds of the formula I and to the use of these compounds as components of liquid-crystalline media. The invention further relates to liquid-crystalline media containing at least one compound of the formula I and to liquid-crystal display elements, in particular electrooptical display elements, containing such media.

For the sake of simplicity, below $A^3$ is a radical of the formula

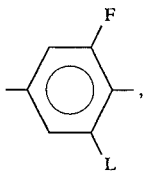

Cyc a 1,4-cyclohexylene radical, Che a 1,4-cyclohexenyl radical, Dio a 1,3-dioxane-2,5-diyl radical, Dit a 1,3-dithiane-2,5-diyl radical, Phe a 1,4-phenylene radical, Pyd a pyridine-2,5-diyl radical, Pry a pyrimidine-2,5-diyl radical and Bi a bicyclo[2.2.2]octylene radical, it being possible for Cyc and/or Phe to be unsubstituted or mono- or disubstituted by F or CN. L is preferably F. Y is preferably F.

$A_1$ and $A_2$ are preferably selected from the group comprising Cyc, Che, Phe, Pyr, Pyd and Dio, preferably only one of the radicals $A_1$ and $A_2$ present in the molecule being Che, Phe, Pyr, Pyd or Dio.

The compounds of the formula I accordingly comprise compounds having two rings of the subformulae Ia and Ib:

| | |
|---|---|
| R—$A^2$—$A^3$—Q—Y | Ia |
| R—$A^2$—$Z^2$—$A^3$—Q—Y | Ib |

Compounds having three rings of the subformulae Ic to If:

| | |
|---|---|
| R—$A^1$—$A^2$—$A^3$—Q—Y | Ic |
| R—$A^1$—$Z^1$—$A^2$—$Z^2A^3$—Q—Y | Id |
| R—$A^1$—$Z^1$—$A^2$—$A^3$—Q—Y | Ie |
| R—$A^1$—$A^2$—$Z^2$—$A^3$—Q—Y | If | and compounds having four rings of the subformulae Ig to Im.

| | |
|---|---|
| R—$A^1$—$A^1$—$A^2$—$A^3$—Q—Y | Ig |
| R—$A^1$—$Z^1$—$A^1$—$A^2$—$A^3$—Q—Y | Ih |
| R—$A^1$—$A^1$—$Z^1$—$A^2$—$A^3$—Q—Y | Ii |
| R—$A^1$—$A^1$—$A^2$—$Z^1$—$A^3$—Q—Y | Ij |
| R—$A^1$—$Z^1$—$A^1$—$Z^1$—$A^2$—$A^3$—Q—Y | Ik |
| R—$A^1$—$A^1$—$Z^1$—$A^2$—$Z^2$—$A^3$—Q—Y | Il |
| D—$A^1$—$Z^1$—$A^1$—$Z^1$—$A^2$—$Z^2$—$A^3$—Q—Y | Im |

Of these, in particular those of the subformulae Ia, Ib, Ic, Id, Ie, If, Ii and Il are preferred.

The preferred compounds of the subformulae Ia comprise those of the subformulae Iaa to Iah:

| | |
|---|---|
| R—Phe—$A^3$—Q—Y | Iaa |
| R—Phe—$A^3$—Q—Y | Iab |
| R—Dio—$A^3$—Q—Y | Iac |
| R—Pyr—$A^3$—Q—Y | Iad |
| R—Pyd—$A^3$—Q—Y | Iae |
| R—Cyc—$A^3$—Q—Y | Iaf |
| R—Cyc—$A^3$—Q—Y | Iag |
| R—Che—$A^3$—Q—Y | Iah |

Of these, those of the formulae Iaa, Iab, Iac, Iad, Iaf and Iag are particularly preferred.

The preferred compounds of the subformula Ib comprise those of the subformulae Iba and Ibb:

| | |
|---|---|
| R—Cyc—CH$_2$CH$_2$—$A^3$—Q—Y | Iba |
| R—Cyc—COO—$A^3$—Q—Y | Ibb |

The preferred compounds of the subformulae Ic comprise those of the subformulae Ica to Ico:

| | |
|---|---|
| R—Phe—Phe—$A^3$—Q—Y | Ica |
| R—Phe—Phe—$A^3$—Q—Y | Icb |
| R—Phe—Dio—$A^3$—Q—Y | Icc |
| R—Cyc—Cyc—$A^3$—Q—Y | Icd |
| R—Phe—Cyc—$A^3$—Q—Y | Ice |
| R—Cyc—Cyc—$A^3$—Q—Y | Icf |
| R—Pyd—Phe—$A^3$—Q—Y | Icg |
| R—Pyr—Phe—$A^3$—Q—Y | Ich |
| R—Phe—Pyr—$A^3$—Q—Y | Ici |
| R—Cyc—Pyr—$A^3$—Q—Y | Icj |
| R—Cyc—Phe—$A^3$—Q—Y | Ick |
| R—Cyc—Phe—$A^3$—Q—Y | Icl |
| R—Dio—Phe—$A^3$—Q—Y | Icm |
| R—Che—Phe—$A^3$—Q—Y | Icn |
| R—Phe—Che—$A^3$—Q—Y | Ico |

Of these, those of the formulae Ica, Icc, Icd, Ice, Ici and Icj are particularly preferred.

The preferred compounds of the subformula Id comprise those of the subformulae Ida to Idm:

| | |
|---|---|
| R—Phe—$Z^1$—Phe—$Z^1$—$A^3$—Q—Y | Ida |

| | |
|---|---|
| R—Phe—Z¹—Phe—Z¹—A³—Q—Y | Idb |
| R—Phe—Z¹—Dio—Z¹—A³—Q—Y | Idc |
| R—Cyc—Z¹—Cyc—Z¹—A³—Q—Y | Idd |
| R—Cyc—Z¹—Cyc—Z¹—A³—Q—Y | Ide |
| R—Pyd—Z¹—Phe—Z¹—A³—Q—Y | Idf |
| R—Phe—Z¹—Pyd—Z¹—A³—Q—Y | Idg |
| R—Pyr—Z¹—Phe—Z¹—A³—Q—Y | Idh |
| R—Phe—Z¹—Pyr—Z¹—A³—Q—Y | Idi |
| R—Phe—Z¹—Cyc—Z¹—A³—Q—Y | Idj |
| R—Cyc—Z¹—Phe—Z¹—A³—Q—Y | Idk |
| R—Cyc—Z¹—Phe—Z¹—A³—Q—Y | Idl |
| R—Dio—Z¹—Phe—Z¹—A³—Q—Y | Idm |

The preferred compounds of the subformulae Ie comprise those of the subformulae Iea to Iel:

| | |
|---|---|
| R—Pyr—Z¹—Phe—A³—Q—Y | Iea |
| R—Dio—Z¹—Phe—A³—Q—Y | Ieb |
| R—Phe—Z¹—Phe—A³—Q—Y | Iec |
| R—Cyc—Z¹—Phe—A³—Q—Y | Ied |
| R—Cyc—Z¹—Phe—A³—Q—Y | Iee |
| R—Phe—Z¹—Cyc—A³—Q—Y | Ief |
| R—Cyc—Z¹—Cyc—A³—Q—Y | Ieg |
| R—Cyc—Z¹—Cyc—A³—Q—Y | Ieh |
| R—Phe—Z¹—Dio—A³—Q—Y | Iei |
| R—Pyd Z¹—Phe—A³—Q—Y | Iej |
| R—Phe—Z¹—Pyr—A³—Q—Y | Iek |
| R—Cyc—Z¹—Pyr—A³—Q—Y | Iel |

The preferred compounds of the subformulae If comprise those of the subformulae Ifa to Ifr:

| | |
|---|---|
| R—Pyr—Phe—Z¹—A³—Q—Y | Ifa |
| R—Pyr—Phe—OCH₂—A³—Q—Y | Ifb |
| R—Phe—Phe—Z¹—A³—Q—Y | Ifc |
| R—Phe—Phe—OOC—A³—Q—Y | Ifd |
| R—Phe—Phe—Z¹—A³—Q—Y | Ife |
| R—Cyc—Cyc—Z¹—A³—Q—Y | Iff |
| R—Cyc—Cyc—Z¹—A³—Q—Y | Ifg |
| R—Cyc—Cyc—CH₂CH₂—A³—Q—Y | Ifh |
| R—Pyd—Phe—Z¹—A³—Q—Y | Ifi |
| R—Dio—Phe—Z¹—A³—Q—Y | Ifj |
| R—Phe—Cyc—Z¹—A³—Q—Y | Ifk |
| R—Phe—Cyc—Z¹—A³—Q—Y | Ifl |
| R—Phe—Pyd—Z¹—A³—Q—Y | Ifm |
| R—Che—Phe—Z¹—A³—Q—Y | Ifn |
| R—Phe—Che—Z¹—A³—Q—Y | Ifo |
| R—Cyc—Phe—Z¹—A³—Q—Y | Ifp |
| R—Cyc—Phe—OOC—A³—Q—Y | Ifq |
| R—Cyc—Phe—Z¹—A³—Q—Y | Ifr |

In the compounds of the formulae above and below, Y is preferably F.

R is preferably alkyl, furthermore alkoxy. $A^1$ and/or $A^2$ are preferably Phe, Cyc, Che, Pyr or Dio. Preferably, the compounds of the formula I do not contain more than one of the radicals Bi, Pyd, Pyr, Dio or Dit.

Compounds of the formula I and of all subformulae in which $A^1$ and/or $A^2$ is 1,4-phenylene which is mono- or disubstituted by F or monosubstituted by CN and also preferred. They are in particular 2-fluoro-1,4-phenylene, 3-fluoro-1,4-phenylene and 3,5-difluoro-1,4-phenylene. In a particularly preferred embodiment, $A^2$ is 3,5-difluoro-1,4-phenylene and m is 1 or 2.

$Z^1$ and $Z^2$ are preferably a single bond, —CO—O—, —O—CO— and —CH₂CH₂—, and secondly preferably —CH₂O— and —OCH₂—.

If one of the radicals $Z^1$ and $Z^2$ is —(CH₂)₄— or —CH=CH—CH₂CH₂—, the other radical $Z^1$ or $Z^2$ (if present) is preferably the single bond.

Preferred compounds of this type correspond to the subformula I'

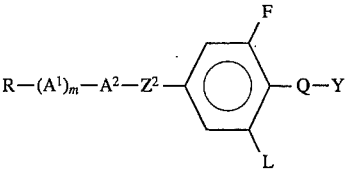

in which $Z^2$ is —(CH₂)₄— or —CH=CH—CH₂CH₂— and R, $A^1$, $A^2$, m, L, Q and Y have the meaning indicated in formula I. The preferred meanings for R, $A^1$, $A^2$, m, l, Q and Y also correspond to those for the compounds of the formula I.

m is preferably 1 or 0, in particular preferably 0.

An alkyl radical and/or alkoxy radical R can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, penadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxa-hexyl, 2-, 3-, 4-, 5- or 6-oxaheptyl, 2-, 3-, 4-, 5-, 6- or 7-oxaoctyl, 2-, 3-, 4-, 5-, 6-, 7 or 8-oxanoyl, 2-, 3-, 4-, 5-, 6-, 7-, 8- or 9-oxadecyl.

An alkyl radical R in which a CH₂ group is replaced by —CH=CH — can be straight-chain or branched. It is preferably straight-chain and has 2 to 10 carbon atoms. Accordingly, it is in particular vinyl, prop-1-, or prop-2-enyl, but-1-, but-2- or but-3-enyl, pent-1-, pent-2-, pent-3- or pent-4-enyl hex-1-, hex-2, hex-3-, hex-4- or hex-5-enyl, hept-1-, hept-2-, hept-3-, hept-4-, hept-5- or hept-6-enyl, oct-1-, oct-2-, oct-3-, oct-4-, oct-5-, oct-6- or oct-7-enyl, non-1-, non-2-, non-3-, non-4-, non-5-, non-6-, non-7- or non-8-enyl, dec-1-, dec-2-, dec-3-, dec-4-, dec-5-, dec-6-, dec-7-, dec-8- or dec-9-enyl.

In an alkyl radical R in which one CH$_2$ group is replaced by —O— and by —CO—, these groups are preferably adjacent. Accordingly, they contain on acyloxy group —CO—O— or one oxycarbonyl group —O—CO—. Preferably, these are straight-chain and have 2 to 6 carbon atoms.

Accordingly, they are in particular acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)butyl.

An alkyl radical R in which one CH$_2$ group is replaced by unsubstituted or substituted —CH═CH— and one adjacent CH$_2$ group by CO or CO—O or O—CO— can be straight-chain or branched. It is preferably straight-chain and has 4 to 13 carbon atoms. Accordingly it is in particular acryloyloxymethyl, 2-acryloyloxymethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl, 9-methacryloyloxynonyl.

An alkyl or alkenyl radical R which is monosubstituted by CN or CF$_3$ is preferably a straight-chain radical and the substitution by CN or CF$_3$ is in the Ω-position.

An alkyl or alkenyl radical R which is at least monosubstitued by halogen is preferably a straight-chain radical and halogen is preferably F or Cl. In the case of multiple substitution, halogen is preferably F. The resulting radicals also include perfluorinated radicals.

In the case of monosubstitution, the fluorine or chlorine substituent may be in any desired position, but is preferably in the Ω-position.

Compounds of the formula I containing wing groups R suitable for polymerization reactions are suitable for preparing liquid-crystalline polymers.

Compounds of the formula I having branched wing groups R can occasionally be of importance due to better solubility in the conventional liquid-crystalline base materials, but in particular as chiral doping substances, provided they are optically active. Smectic compounds of this type are suitable as components for ferroelectric materials.

Compounds of the formula I having S$_A$ phases are suitable, for example, for thermally addressed displays.

Branched groups of this type, as a rule, do not contain more than one chain branching. Preferred branched radicals R are isopropyl, 2-butyl (=1-methylpropyl), isobutyl, (=2-methylpropyl, 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy.

An alkyl radical R in which two or more CH$_2$ groups are replaced by —O— and/or —CO—O— can be straight-chain or branched. It is preferably branched and has 3 to 12 carbon atoms. Accordingly, it is in particular bis(carboxy)methyl, 2,2-bis(carboxy)ethyl, 3,3-bis(carboxy)propyl, 4,4-bis(carboxy)butyl, 5,5-bis(carboxy)pentyl, 6,6-bis(carboxy)hexyl, 7,7-bis(carboxy)heptyl, 8,8-bis(carboxyoctyl, 9,9-bis(carboxy)nonyl, 10,10-bis(carboxy)decyl, bis(methoxycarbonyl)methyl 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl, 5,5-bis(ethoxycarbonyl)hexyl.

Compounds of the formula I containing wing groups R suitable for polycondensations are suitable for preparing liquid-crystalline polycondensation products.

Formula I comprises not only the racemates of these compounds but also the optical antipodes and mixtures thereof.

Of these compounds of the formula I and their subformulae, those are preferred in which at least one of the radicals contained therein has one of the preferred meanings mentioned.

In the compounds of the formula I, those stereoisomers are preferred in which the rings Cyc and piperidine are trans-1,4-disubstituted. Those of the abovementioned formulae containing one or more groups Pyd, Pyr and/or Dio each comprise the two isomers in the 2,5 position.

A few very particularly preferred smaller groups of compounds are those of the subformulae I1 to I11:

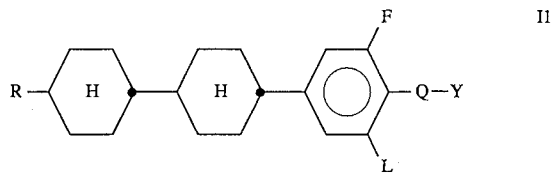

I1

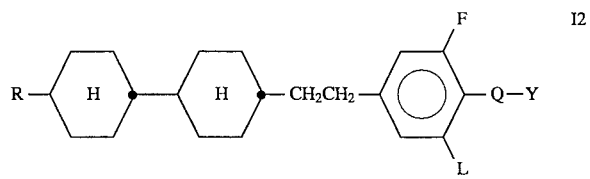

I2

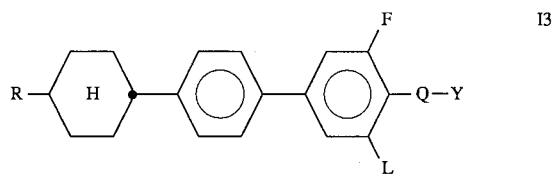

I3

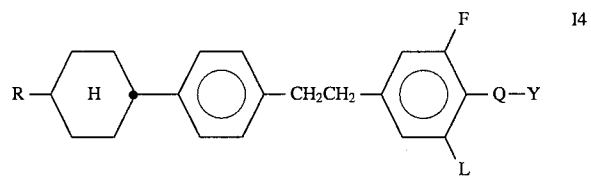

I4

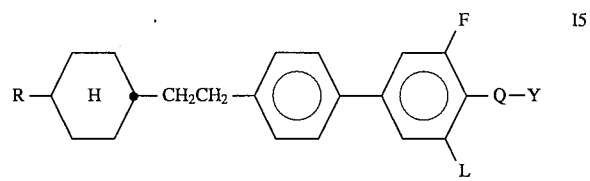

I5

-continued

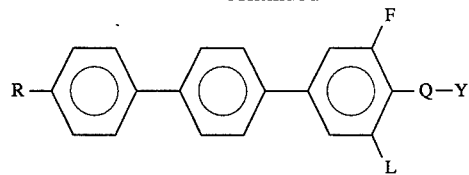
I6

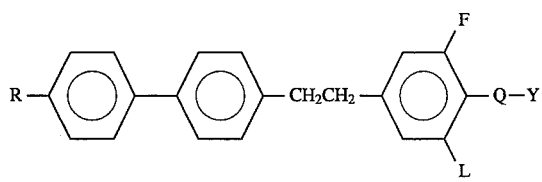
I7

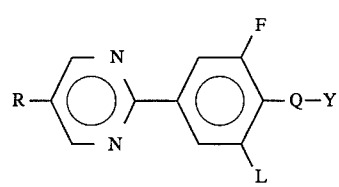
I8

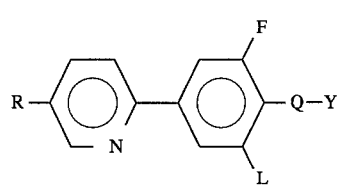
I9

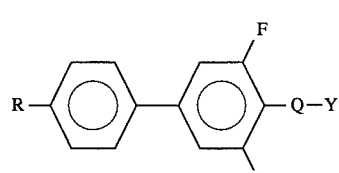
I10

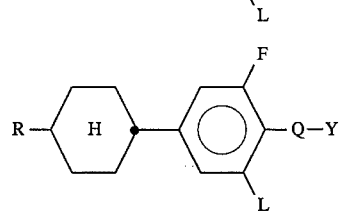
I11

The 1,4-cyclohexenylene group preferably has the following structures:

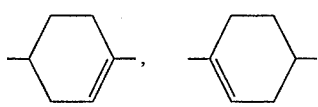

The compounds of the formula I are prepared by methods known per se, such as are described in the literature (e.g. in the standard works such as Houben-Weyl, Methoden der Organischen Chemie [Methods of Organic Chemistry], Georg-Thieme-Verlag, Stuttgart Vol. IX, p. 867 ff.), under reaction conditions known and suitable for the reactions mentioned.

It is also possible to use variations known per se and not mentioned here in more detail.

The compounds according to the invention can be prepared, for example, by metalating a compound of the formula II

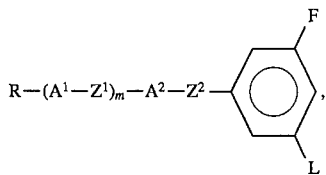
II in which R, $A^1$, $A^2$, $Z^1$, $Z^2$ and m have the meaning mentioned, in accordance with the reaction scheme below and then reacting the product with a suitable electrophile:

Scheme 1

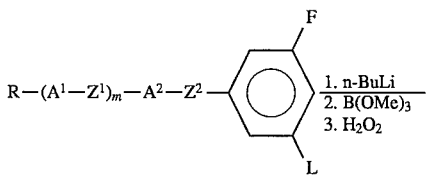

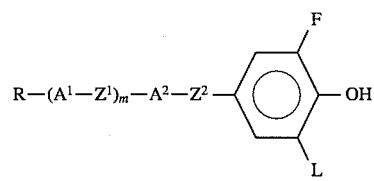

The target products where Q is $OCF_2$ or OCHF can be obtained from the phenol formed by known methods, for example by reaction with chlorodifluoromethane or carbon tetrachloride/HF.

Further methods of synthesis are evident to one skilled in the art. For example, 1,3-difluorobenzene compounds appropriately substituted in the 5 position or mono-fluorinated analogues (L=H) can be converted according to the above scheme to the 2-$OCF_2$Y-1,3-difluoro compounds or to the mono-fluorinate analogues (L=H) and the radical R—($A^1$—$Z^1$)$_m$—$A^2$—$Z^2$ can then be introduced via reactions customary in liquid-crystal chemistry (e.g. esterification, etherification or coupling reactions, for example as described in E. Poetsch, Kontakte (Darmstadt) 1988 (2), p. 15).

Scheme 2

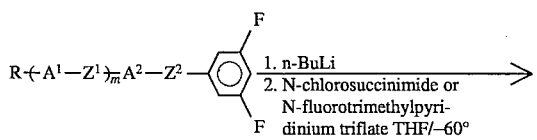

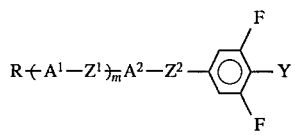

Further methods of synthesis are evident to one skilled in the art. For example, 1,3-difluorobenzene compounds appropriately substituted in the 5 position can be converted in accordance with the above scheme to the 2-Y-1,3-difluoro compounds and the radical R—($A^1$—$Z^1$)$_m$—$A^2$—$Z^2$ can then be lead (sic) by reactions customary in liquid-crystal chemistry (e.g. esterification, etherification or coupling reactions, for example as described in E. Poetsch, Kontakte (Darmstadt) 1988 (2), p. 15).

The compounds according to the invention of the formula I in which L is F and Q—Y is $CF_3$ can be prepared by metalation of the unsubstituted 3,5-difluorophenyl compounds where n-BuLi, followed by reaction with iodine and reaction of the iodine compound with sodium trifluoroacetate according to the following scheme:

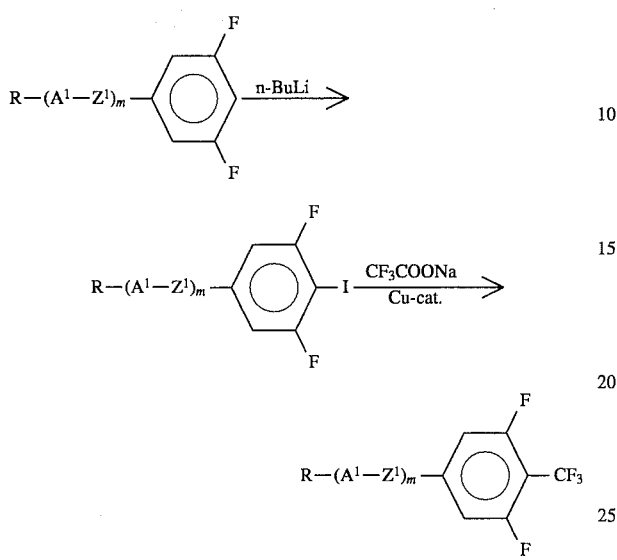

The compounds according to the invention where L is H and Q—Y is $CF_3$ can be prepared by converting 3-fluoro-4-iodobromobenzene to the benzotrifluoride compound with $CF_3COONa$ and then introducing the radical $R—(A^1—Z^1)_m$, for example by conventional coupling reactions:

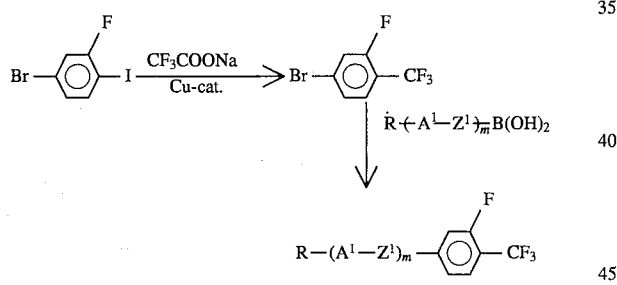

The compounds of the formula II can be prepared, for example, according to the following synthetic schemes:

Scheme 3

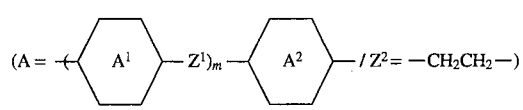

Scheme 3

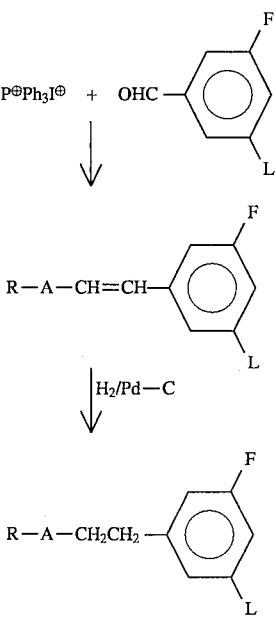

Scheme 4
$(A = -(A^1—Z^1)_m—A^2—/Z^2 = $ single bond$)$

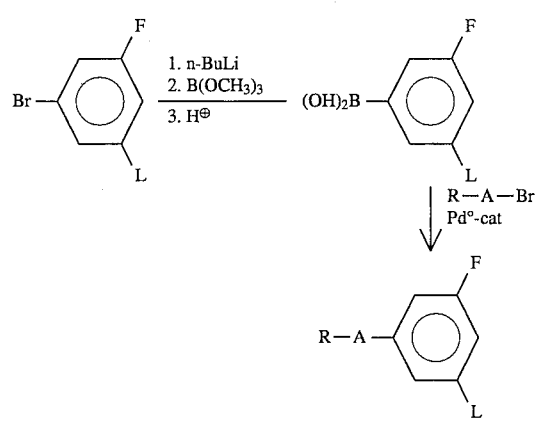

Scheme 5

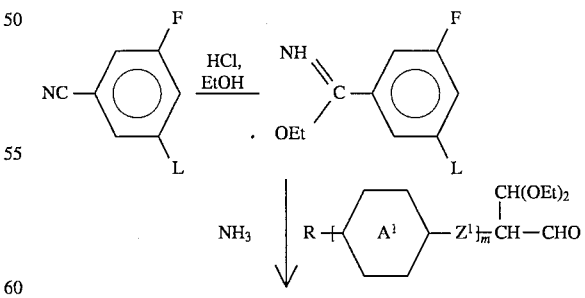

Scheme 5

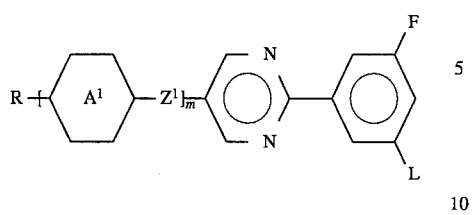

Scheme 6

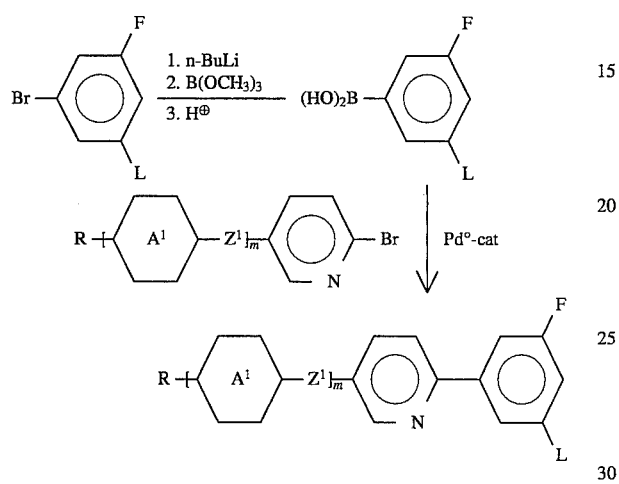

Scheme 7

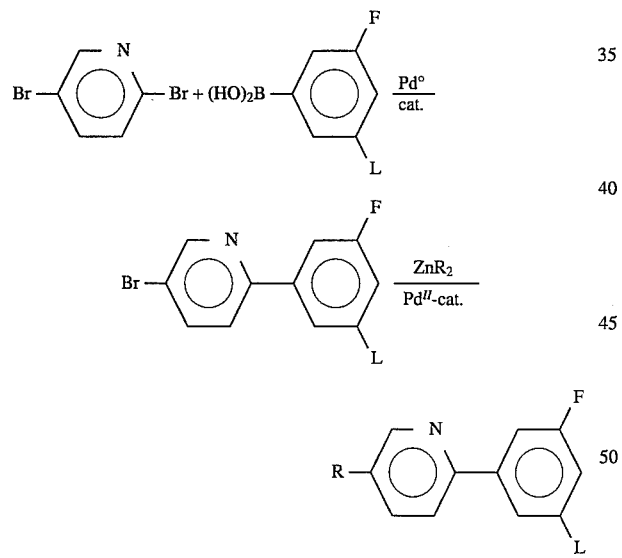

The starting materials are either known or can be prepared in analogy with known compounds.

Esters of the formula I can also be obtained by esterification of the corresponding carboxylic acids (or reactive derivatives thereof) with alcohols or phenols (or reactive derivatives thereof) or by the DCC method (DCC=dicyclohexylcarbodiimide).

The corresponding carboxylic acids and alcohols and phenols are known or can be prepared in analogy with known processes.

The synthesis of a few particularly preferred compounds is detailed below:

Scheme 8

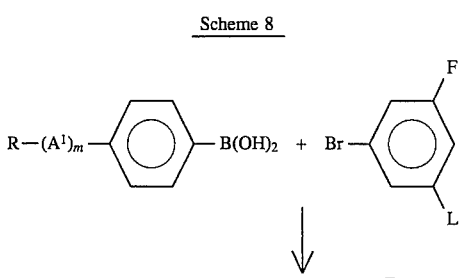

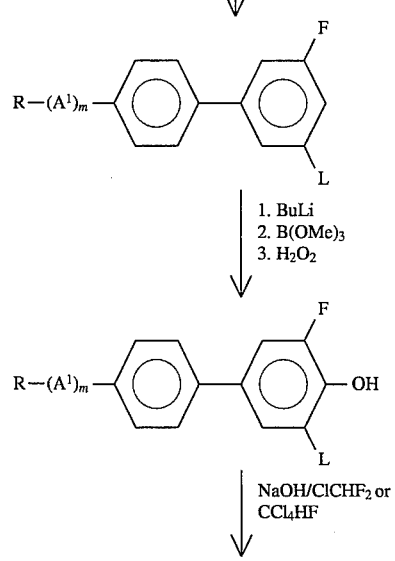

(X = OCHF$_2$, —OCClF$_2$ or —OCF$_3$)

Scheme 9

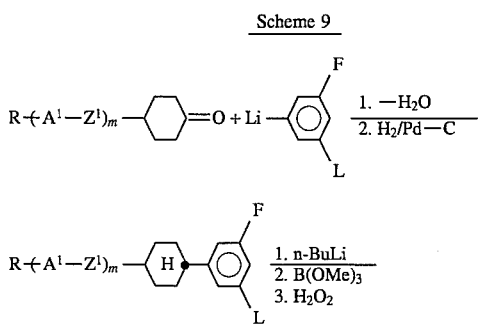

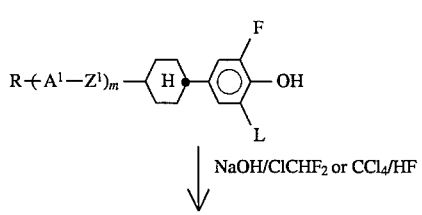

NaOH/ClCHF$_2$ or CCl$_4$/HF

-continued
Scheme 9
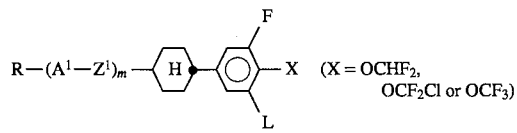
Scheme 10
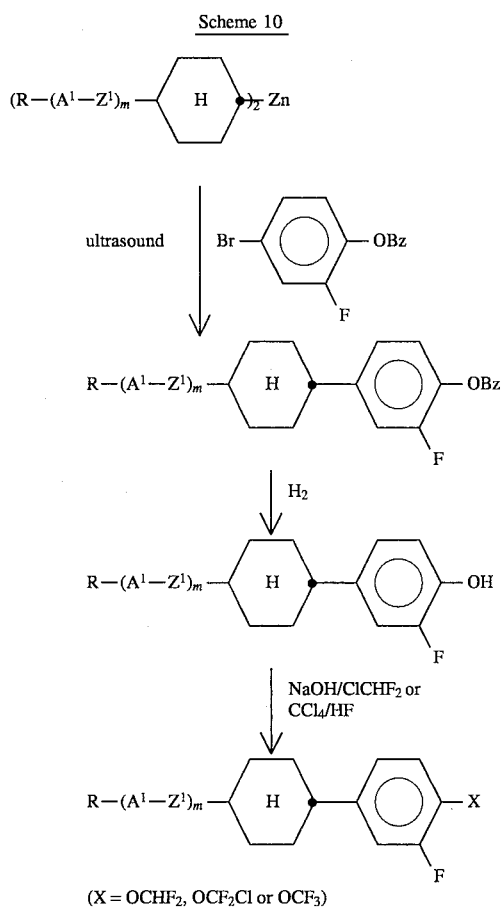
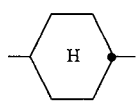
Scheme 11
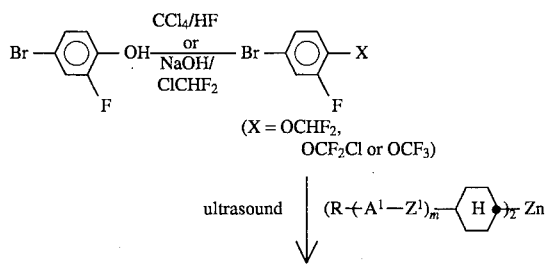
-continued
Scheme 11
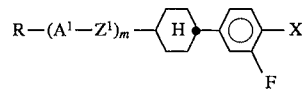
Scheme 12
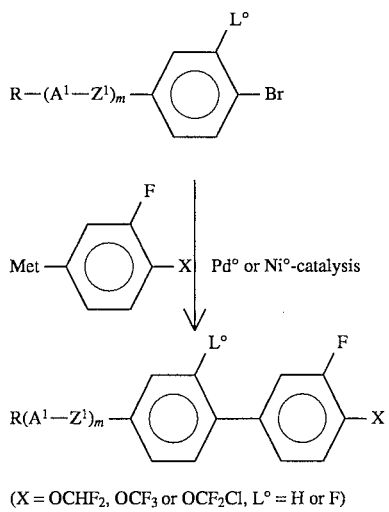
Scheme 13
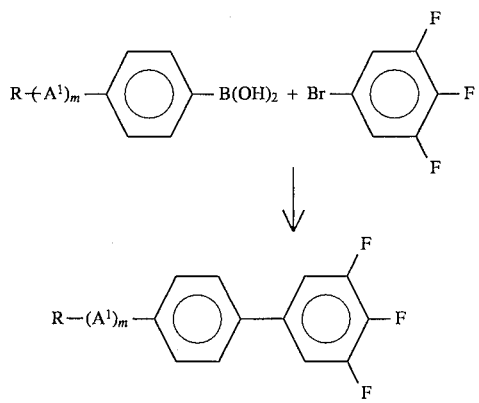
Scheme 14
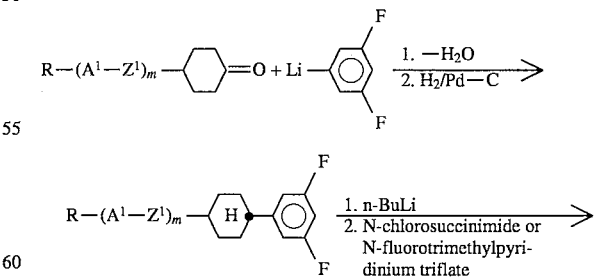

5,487,845
17
-continued
Scheme 14
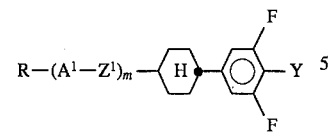
Scheme 15
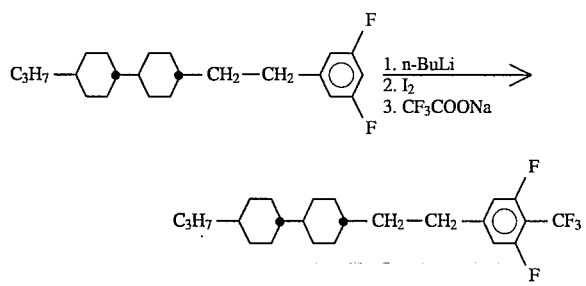
Scheme 16
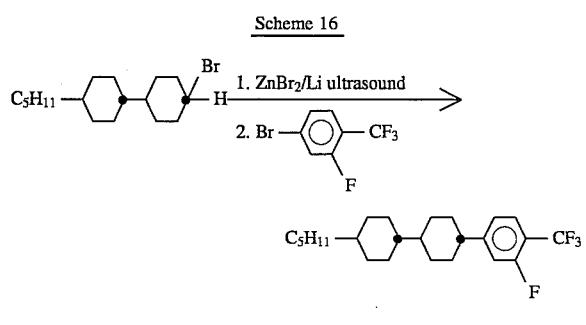
Scheme 17
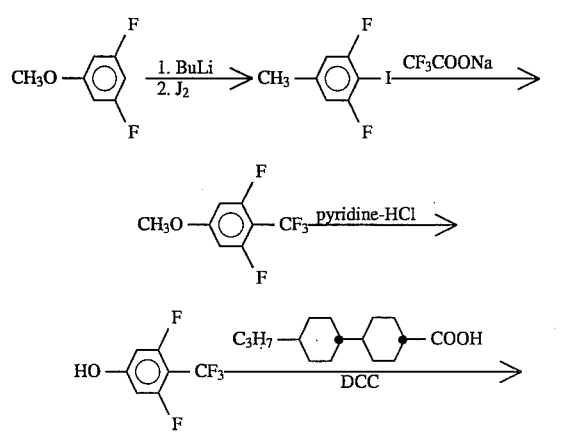
Scheme 18
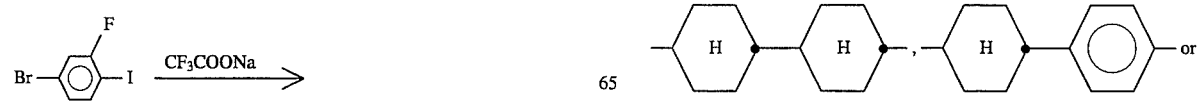
18
-continued
Scheme 18
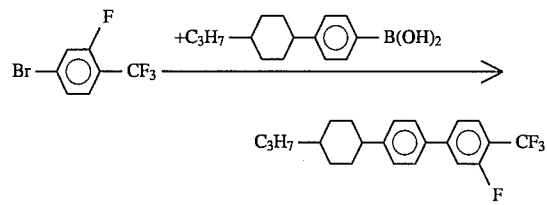
Scheme 19
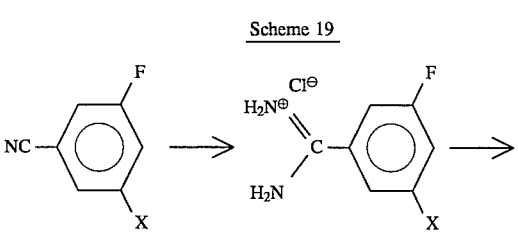
Scheme 20
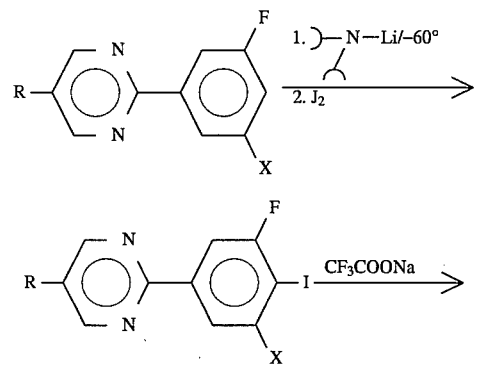

-continued
Scheme 20

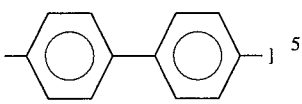

Scheme 21

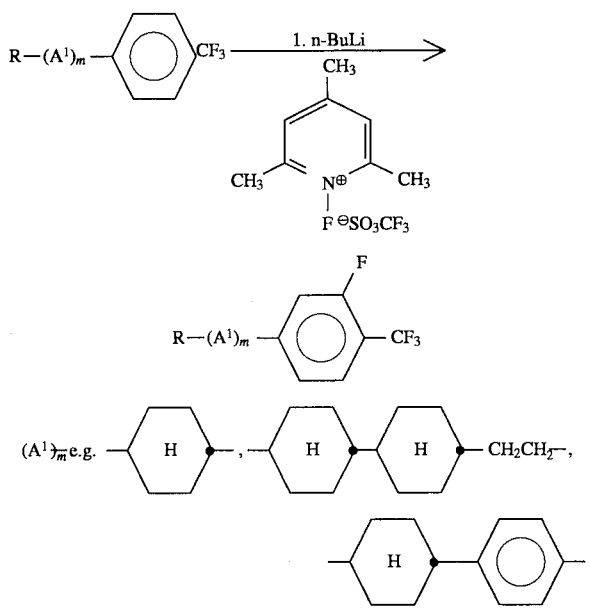

Esters of the formula I can also be obtained by esterification of corresponding carboxylic acids (or their reactive derivatives) with alcohols or phenols (or their reactive derivatives) or by the DCC method (DCC= dicyclohexylcarbodiimide).

The corresponding carboxylic acids and alcohols or phenols are known or can be prepared in analogy to known processes.

In a further process for the preparation of the compounds of the formula I, an aryl halide is reacted with an olefin in the presence of a tertiary amine and a paladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the coupling reaction to succeed, such as, for example, triethylamine, are also suitable as solvents. Examples of suitable palladium catalyst are palladium salts, in particular Pd(II) acetate, with organic phosphorus(III) compounds, such as, for example, triarylphosphanes. The reaction can be carried out in the presence or absence of an inert solvent at temperatures between about 0° and 150°, preferably between 20° and 100°; examples of suitable solvents are nitriles, such as acetonitriles (sic), or hydrocarbons, such as benzene or toluene. The aryl halides and olefins which are used as starting materials are commercially available in large numbers or can be prepared by processes known from the literature, for example by halogenation of the corresponding parent compounds or by elimination reactions performed on the corresponding alcohols or halides.

In this manner, it is, for example, possible to prepare stilbene derivatives. The stilbenes can furthermore be prepared by reaction of a 4-substituted benzaldehyde with the corresponding phosphorus ylide, according to Wittig. However, it is also possible to prepare tolans of the formula I by using monosubstituted acetylene instead of the olefin (Synthesis 627 (1980) or Tetrahedron Lett. 27, 1171 (1986)).

Furthermore, in order to couple aromatics, aryl halides can be reacted with aryltin compounds. These reactions are preferably carried out with the addition of a catalyst, such as, for example, a palladium(O) complex, in inert solvents, such as hydrocarbons, at elevated temperatures, for example in boiling xylene, under an inert gas.

Coupling reactions of alkynyl compounds with aryl halides can be carried out analogously to the process described in A. O. King, E. Negishi, F. J. Villani and A. Silveira in J. Org. Chem. 43, 358 (1978).

Tolans of the formula I can also be prepared via the Fritsch-Buttenberg-Wiechell rearrangement (Ann. 279, 319, 1984), in which 1,1-diaryl-2-halogenoethylenes are rearranged to diarylacetylene in the presence of strong bases.

Tolans of the formula I can also be prepared by brominating the corresponding stilbenes and then subjecting the product to dehydrohalogenation. It is possible to sue variations known per se of this reaction not mentioned here in more detail.

Ethers of the formula I can be obtained by etherification of the corresponding hydroxy compounds, preferably of the corresponding phenols, in which the hydroxy compound is preferably first converted to the corresponding metal derivative, for example by treatment with NaH, NaNH$_2$, NaOH, KOH, Na$_2$CO$_3$ or K$_2$CO$_3$ to the corresponding alkali metal alcoholate or alkali metal phenolate. This derivative can then be reacted with the corresponding alkyl halide, alkyl sulfonate or dialkyl sulfate, preferably in an inert solvent, such as, for example, acetone, 1,2-dimethoxyethane, DMF or dimethyl sulfoxide or even with excess aqueous or aqueous-alcoholic NaOH or KOH at temperatures between about 20° and 100°.

The starting materials are either known or can be prepared in analogy to known compounds.

The compounds of the formula I' where $Z^2 = -(CH_2)_4-$ can be prepared by the following scheme:

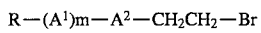

chain alongation by means of malonic ester

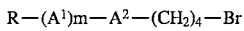

ZnBr$_2$/Li ultrasound

-continued

[R—(A¹)m—A²—(CH₂)₄]₂—Zn

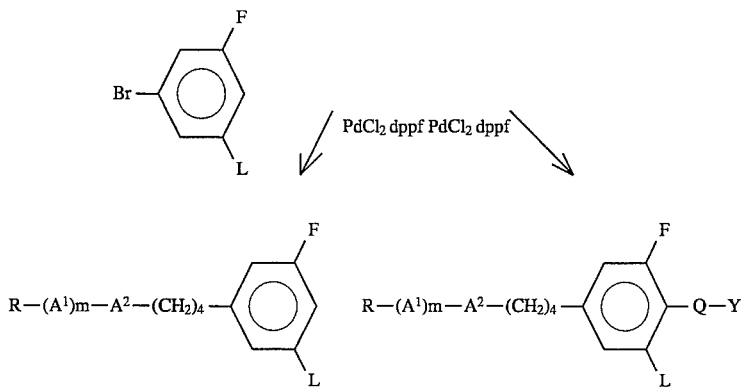

In the Pd(II)-catalyzed coupling reaction, either the target product I' is formed directly or a precursor in which the radical —Q—Y is introduced completely analogously to the above methods for compounds of formula I.

The compounds of the formula I' where $Z^2$=—CH=CH—CH₂CH₂— can be prepared until (sic) Wittig as in the following scheme:

R—(A¹)ₘ—A²—CH₂—P⊕Ph₃Br⊖

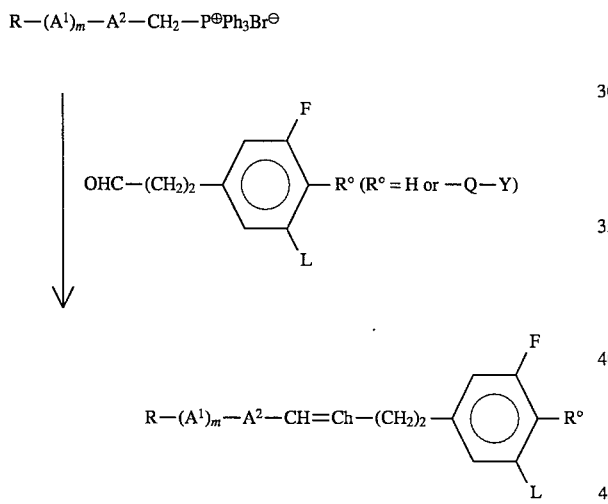

The preferred trans isomers can be prepared by sic the isomerization methods known from the literature. The precursors where R°=H which may be obtained are converted into the compounds of the formula I' completely analogously to the precursors of the compounds of the formula I by introducing the radical —Q—Y.

The aldehydes can be obtained by Heck reaction of appropriately substituted 1-bromo-3-fluorobenzene derivatives with alkyl alcohol.

The liquid-crystalline media according to the invention preferably contain, in addition to one or more compounds according to the invention, 2 to 40, in particular 4 to 30 further components. These media very particularly preferably contain, in addition to one or more compounds according to the invention, 7 to 25 components. These further components are preferably selected from nematic or nematogenic (monotropic or isotropic) substances, in particular substances from the classes of azoxybenzenes, benzylideneaniline, biphenyls, terphenyls, phenyl or cyclohexyl benzoates, phenyl or cyclohexy cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates or cyclohexylcyclohexanecarboxylates, phenylcyclohexanes, cyclohexylbiphenyls, phenylcyclohexylcyclohexanes, cyclohexylcyclohexanes, cyclohexylcyclohexylcyclohexenes, 1,4-bis(cyclohexyl)benzenes, 4,4'-bis(cyclohexyl)biphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl- 2-(4-phenylcyclohexyl)ethanes, 1-cyclohexyl-2-biphenylethanes, 1-phenyl-2-cyclohexylphenylethanes, halogenated or unhalogenated stilbenes, benzyl phenyl ethers, tolans and substituted cinammic acids. The 1,4-phenylene groups in these compounds can also be fluorinated.

The most important compounds which are suitable as further components of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH₂CH₂—E—R" | 4 |
| R'—L—C≡C—E—R" | 5 |

In the formulae 1, 2, 3, 4 and 5, L and E, which can be identical or different, in each case independently of one another, are a divalent radical from the group formed by —Phe—, —Cyc—, —Phe—Phe—, —Phe—Cyc—, —Cyc—Cyc—, —Pry—, —Dio—, —G—Phe— and —G—Cyc— and their mirror images, in which Phe is unsubstituted or fluorine-substituted 1,4-phenylene, Cyc is trans-1,4-cyclohexylene or 1,4-cyclohexenylene, Pyr is pryimidine-2,5-dioxane-2,5-diyl and G is 2-(trans- 1,4-cyclohexyl)ethyl, pyrimidine-2,5-diyl, pyridine- 2,5-diyl or 1,3-dioxane-2,5-diyl.

Preferably, one of the radicals L and E is Cyc, Phe or Pyr. E is preferably Cyc, Phe or Phe—Cyc. The media according to the invention preferably contain one or more components selected from the compounds of the formulae 1, 2, 3, 4, and 5, in which L and E are selected from the group comprising Cyc, Phe and Pyr and simultaneously one or more components selected from the compounds of the formulae 1, 2, 3, 4, and 5, in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and, if desired, one or more components selected from the compounds of the formulae 1, 2, 3, 4 and 5, in which the radicals L and E are selected from the group —Phe—Cyc, —Cyc—Cyc—, —G—Phe— and —G—Cyc—.

R' and R", in a smaller subgroup of the compounds of the formulae 1, 2, 3, 4 and 5, are in each case independently of one another alkyl, alkenyl, alkoxy, alkoxyalkyl, alkenyloxy or alkanoyloxy having up to 8 carbon atoms. In the following, this smaller subgroup is named group A and the compounds are denoted by the subformulae 1a, 2a, 3a, 4a and 5a. In most of these compounds, R' and R" are different from one another, one of these radicals usually being alkyl, alkenyl, alkoxy or alkoxyalkyl.

In another smaller subgroup of the compounds of the formulae 1, 2, 3, 4 and 5 named group B, R" is —F, —Cl —NCS or —$(O)_iCH_{3-(k+1)}F_kCl_1$, where i is 0 or 1 and k+1 is 1, 2 or 3; the compounds in which R" has this meaning are denoted by the subformulae 1b, 2b, 3b, 4b and 5b. Particularly preferred compounds are those of the subformulae 1b, 2b, 3b, 4b and 5b in which R" has the meaning —F, —Cl, —NCS, —$CF_3$—$OCHF_2$ or —$OCF_3$.

In the compounds of the subformulae 1b, 2b, 3b, 4b and 5b, R' has the meaning indicated for the compounds of the subformulae 1a–5a and is preferably alkyl, alkenyl, alkoxy or alkoxyalkyl.

In a further smaller subgroup of the compounds of the formulae 1, 2, 3, 4 and 5, R" is —CN; this subgroup is denoted as group C in the following and the compounds of this subgroup are correspondingly described by subformulae 1c, 2c, 3c, 4c and 5c. In the compounds of the subformulae 1c, 2c, 3c, 4c and 5c, R' has the meaning indicated for the compounds of the subformulae 1a–5a and is preferably alkyl, alkoxy or alkenyl.

In addition to the preferred compounds of the groups A B and C, other compounds of the formulae 1, 2, 3, 4 and 5 having other variants of the intended substituents are also customary. All these substances are obtainable by methods which are known in the literature or in analogy to these.

In addition to compounds of the formula I according to the invention, the media according to the invention preferably contain one or more compounds which are selected from the group A and/or group B and/or group C. The proportions by weight of the compounds of these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50% the sum of the proportions by weight of the compounds of the groups A and/or B and/or C contained in the respective media according to the invention preferably being 5%–90% and in particular 10% to 90%.

The media according to the invention preferably contain 1 to 40%, particularly preferably 5 to 30%, of the compounds according to the invention, Media containing more than 40%, in particular 45 to 90%, of the compounds according to the invention are furthermore preferred. The media preferably contain three, four or five compounds according to the invention.

The media according to the invention are prepared in a manner customary per se. As a rule, the components are dissolved in one another, preferably at elevated temperature. By means of suitable additives, the liquid-crystalline phases according to the invention can be modified in such a manner that they can be used in all previously known types of liquid-crystal display elements. These types of additives are known to one skilled in the art and have been described in detail in the literature (H. Kelker/R. Hatz, Handbook of Liquid Crystals, Verlag Chemie, Weinheim, 1980). For example, pleochroic dyes for preparing coloured guest-host systems or substances for changing the dielectric anistropy, the viscosity and/or the orientation of the nematic phases can be added.

EXAMPLES

The examples which follow are intended to illustrate the invention, without limiting it. Above and below, the percentages given are by weight. All temperature are given in degree Centigrade. M.p. denotes the melting point and c.p. the clear point. Furthermore, C denotes crystalline state, N=the nematic phase, S=the smectic phase and I=the isotropic phase. The numbers between these symbols are the transition temperatures. $\Delta n$ is optical anisotropy (589 nm, 20° C.), and the viscosity ($mm^2$, sec) was determined at 20° C.

In the present application and in the following examples, the structures of the liquid crystal compounds are indicated by acronyms, the transformation into chemical formulae taking place according to the following Tables A and B. All radicals $C_nH_{2n+1}$ and $C_mH_{2m+1}$ are straight-chain alkyl radicals having n or m C atoms. The coding according to Table B is self-evident. In Table A, only the acronym for the basic structure is indicated. In the individual case, a code for the substituents $R^1$, $R^2$, $L^1$ and $L^2$ follows separately from the acronym for the basic structure:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| nT | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nOmFF | $C_nH_{2n+1}$ | $OC_mH_{2m+1}$ | F | F |
| nmF | $C_nH_{2n+1}$ | $C_mH_{2m+1}$ | F | H |
| nCF$_3$ | $C_nH_{2n+1}$ | $CF_3$ | H | H |

-continued
| Code for $R^1$, $R^2$, $L^1$, $L^2$ | $R^1$ | $R^2$ | $L^1$ | $L^2$ |
|---|---|---|---|---|
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nNF | $C_nH_{2n+1}$ | CN | F | H |
| nAm | $C_nH_{2n+1}$ | COOC$_m$H$_{2m+1}$ | H | H |
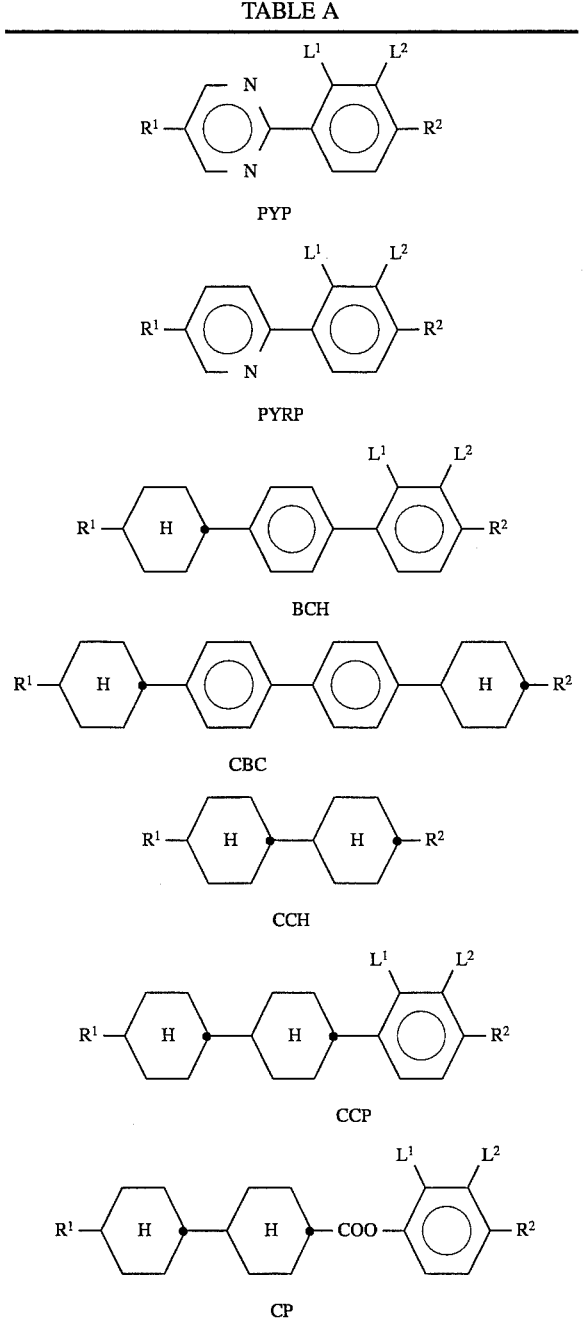
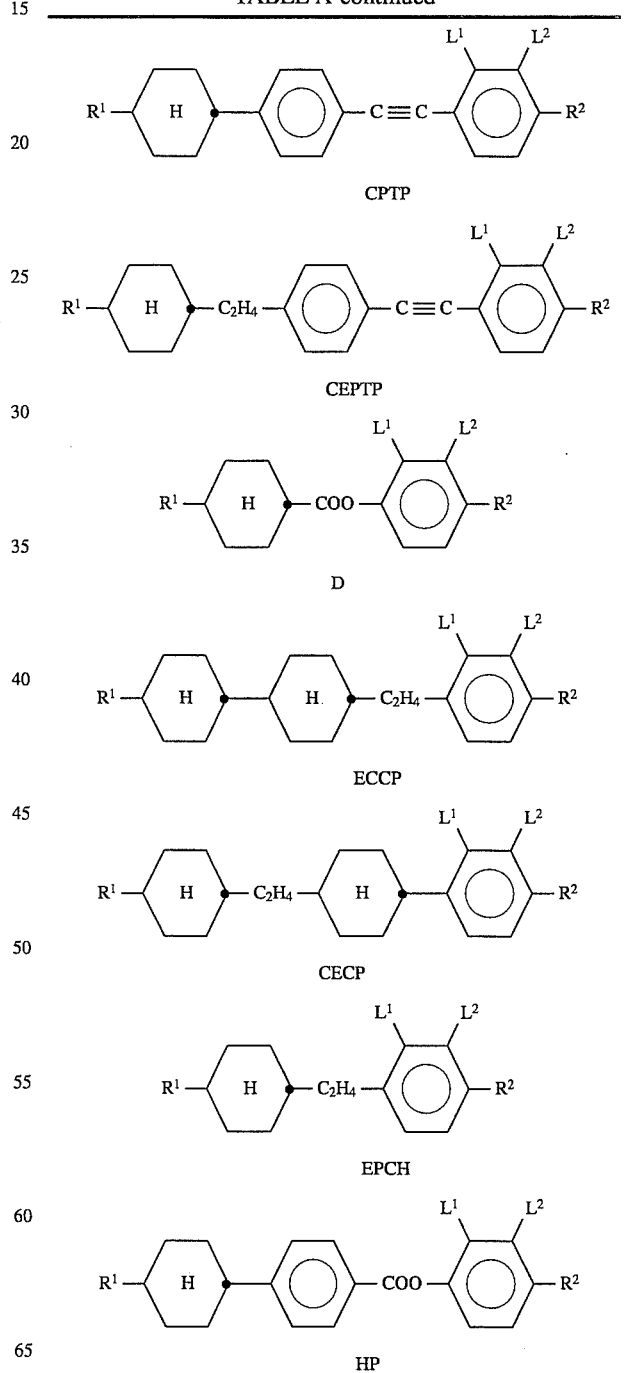

TABLE A-continued

R¹–⟨phenyl⟩–COO–⟨phenyl(L¹,L²)⟩–R²

ME

R¹–⟨cyclohexyl⟩–⟨phenyl(L¹,L²)⟩–R²

PCH

R¹–⟨dioxane⟩–⟨phenyl(L¹,L²)⟩–R²

PDX

R¹–⟨phenyl⟩–C≡C–⟨phenyl(L¹,L²)⟩–R²

PTP

R¹–⟨cyclohexyl⟩–C₂H₄–⟨phenyl⟩–⟨phenyl(L¹,L²)⟩–R²

BECH

R¹–⟨cyclohexyl⟩–⟨phenyl⟩–C₂H₄–⟨phenyl(L¹,L²)⟩–R²

EBCH

R¹–⟨cyclohexyl⟩–⟨phenyl⟩–⟨cyclohexyl⟩–R²

CPC

TABLE B $C_5H_{11}$–⟨phenyl⟩–⟨phenyl⟩–⟨phenyl⟩–CN

T15

$C_nH_{2n+1}$–⟨phenyl⟩–⟨phenyl⟩–CN

K3n

$C_nH_{2n+1}$–O–⟨phenyl⟩–⟨phenyl⟩–CN

M3n

TABLE B-continued $C_nH_{2n+1}$–⟨cyclohexyl⟩–⟨phenyl(F)⟩–⟨phenyl⟩–$C_mH_{2m+1}$

BCH-n.Fm

$C_nH_{2n+1}$–⟨cyclohexyl⟩–$C_2H_4$–⟨phenyl⟩–⟨phenyl(F)⟩–$C_mH_{2m+1}$

Inm

$C_nH_{2n+1}$–⟨cyclohexyl⟩–⟨cyclohexyl⟩–OOC–$C_mH_{2m+1}$

C-nm

$C_2H_5$–CH(CH₃)–CH₂–O–⟨phenyl⟩–⟨phenyl⟩–CN

C15

$C_2H_5$–CH(CH₃)–CH₂–⟨phenyl⟩–⟨phenyl⟩–CN

CB15

$C_nH_{2n+1}$–⟨cyclohexyl⟩–⟨phenyl(F)⟩–⟨phenyl⟩–⟨cyclohexyl⟩–$C_mH_{2m+1}$

CBC-nmF

$C_nH_{2n+1}$–⟨cyclohexyl⟩–⟨cyclohexyl(CN)⟩–$C_mH_{2m+1}$

CCN-nm

$C_nH_{2n+1}$–⟨cyclohexyl⟩–⟨cyclohexyl⟩–COO–⟨phenyl⟩–⟨cyclohexyl⟩–$C_mH_{2m+1}$

CCPC-nm

$C_nH_{2n+1}$–⟨cyclohexyl⟩–⟨cyclohexyl⟩–COO–⟨cyclohexyl⟩–$C_mH_{2m+1}$

CH-nm

$C_nH_{2n+1}$–⟨cyclohexyl⟩–⟨phenyl⟩–OOC–⟨cyclohexyl⟩–$C_mH_{2m+1}$

HD-nm

$C_nH_{2n+1}$–⟨cyclohexyl⟩–⟨phenyl⟩–COO–⟨cyclohexyl⟩–$C_mH_{2m+1}$

HH-nm

$C_nH_{2n+1}$–⟨phenyl⟩–⟨phenyl⟩–⟨cyclohexyl(CN)⟩–$C_mH_{2m+1}$

NCB-nm

$C_nH_{2n+1}$–⟨cyclohexyl⟩–COO–⟨cyclohexyl⟩–$C_mH_{2m+1}$

OS-nm

$C_2H_5$–⟨cyclohexyl⟩–COO–⟨phenyl⟩–⟨phenyl⟩–CN

CHE

$C_nH_{2n+1}$–⟨cyclohexyl⟩–$C_2H_4$–⟨phenyl⟩–⟨phenyl⟩–⟨cyclohexyl⟩–$C_mH_{2m+1}$

ECBC-nm

TABLE B-continued

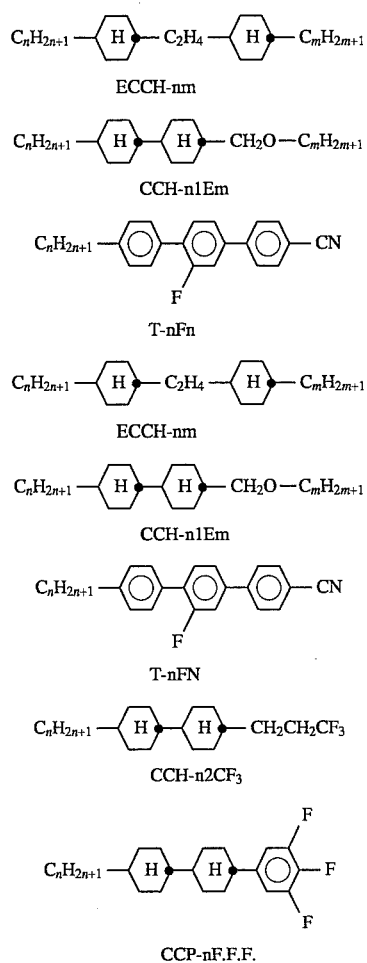

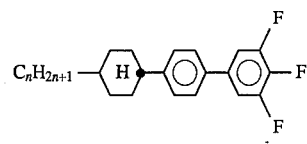

BCH-n.F.F.F

"Conventional work-up" means: if necessary, water is added, the product is extracted with methylene chloride, diethyl ether or toluene, the organic phase is separated off, dried, evaporated, and the product is purified by distillation under reduced pressure or crystallization and/or chromatography. The following abbreviations are used:

| | |
|---|---|
| DAST | Diethylaminosulfur trifluoride |
| DCC | Dicyclohexylcarbodiimide |
| DDQ | Dichlorodicyanobenzoquinone |
| DIBALH | Diisobutylaluminium hydride |
| KOT | Potassium tert.-butoxide |
| THF | Tetrahydrofuran |
| pTSOH | p-Toluenesulfonic acid |
| TMEDA | Tetramethylethylenediamine |

Example 1

0.1 mole of n-BuLi (1.5 in hexane) is added dropwise at about −65° C. to a solution of 0.1 mol of 1-trans-4-trans-4-n-propylcyclohexyl)cyclohexyl-2-(3,5-difluorophenyl)ethane (prepared according to scheme 1) and 0.1 mol of TMEDA in 300 ml of THF. Stirring at this temperature is continued for another 30 minutes, and 0.1 mol of $B(OCH_3)_3$ is added to this mixture at −60° to −70° C. Stirring is continued for another half hour. 0.3 mol of $H_2O_2$ (30%) is added dropwise, during which the temperature should not exceed +40° C. Extractive work-up gives the phenol, which can be purified by crystallization or distillation.

The $OCHF_2$ derivative is obtained from this phenol by introducing $CHClF_2$ into the THF solution of the phenolate. Extractive work-up and conventional purification gives 1-[trans4-(trans-4-n-propylcyclohexyl)cyclohexyl]-2-(4-difluoromethoxy- 3,5-difluorophenyl)ethane.

Examples 2 to 23

The following compounds according to the invention are obtained analogously from the corresponding precursors of the formula II:

| R | $(A^1-Z^1)_m-A^2-Z^2-$ | Q-Y | L |
|---|---|---|---|
| (2) Ethyl | ⟨H⟩-⟨H⟩-CH₂CH₂- | OCHF₂ | F |
| (3) n-Butyl | ⟨H⟩-⟨H⟩-CH₂CH₂- | OCHF₂ | F |
| (4) n-Pentyl | ⟨H⟩-⟨H⟩-CH₂CH₂- | OCHF₂ | F |

-continued
| R | $(A^1-Z^1)_m-A^2-Z^2-$ | Q—Y | L |
|---|---|---|---|
| (5) n-Heptyl | 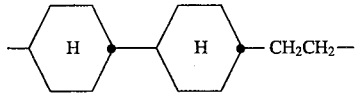 | OCHF$_2$ | F |
| (6) Ethyl | 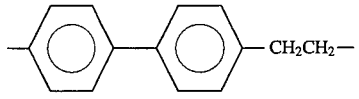 | OCHF$_2$ | F |
| (7) Methoxy | 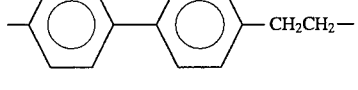 | OCHF$_2$ | F |
| (8) Ethoxy |  | OCHF$_2$ | F |
| (9) n-Propyl |  | OCHF$_2$ | F |
| (10) n-Pentyl | 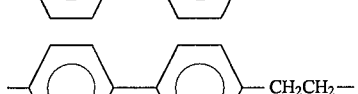 | OCHF$_2$ | F |
| (11) Methoxymethyl | 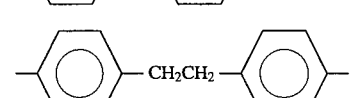 | OCHF$_2$ | F |
| (12) n-Propyl | 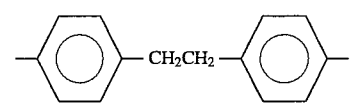 | OCHF$_2$ | F |
| (13) n-Pentyl | 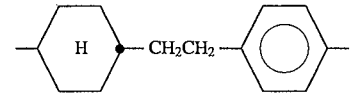 | OCHF$_2$ | F |
| (14) n-Propyl | 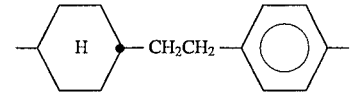 | OCHF$_2$ | F |
| (15) n-Pentyl | 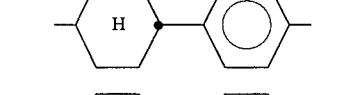 | OCHF$_2$ | F |
| (16) n-Propyl |  | OCHF$_2$ | F |
| (17) n-Butyl |  | OCHF$_2$ | F |
| (18) n-Pentyl | 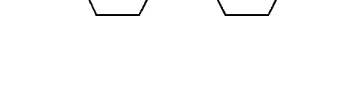 | OCHF$_2$ | F |
| (19) n-Propyl |  | OCHF$_2$ | F |

| | R | $(A^1-Z^1)_m-A^2-Z^2-$ | Q—Y | L | |
|---|---|---|---|---|---|
| (20) | n-Pentyl | Ph—Ph— | OCHF₂ | F | |
| (21) | n-Propyl | Cy(H)—Cy(H)— | OCHF₂ | F | C61N128I |
| (22) | n-Butyl | Cy(H)—Cy(H)— | OCHF₂ | F | |
| (23) | n-Pentyl | Cy(H)—Cy(H)— | OCHF₂ | F | |

Example 24

2 mol of anhydrous hydrofluoric acid is poured into an autoclave which has been cooled to 0° C. A mixture of 0.18 mol of carbon tetrachloride and 0.06 mol of 1-[trans-4-(trans-4-n-propylhexyl)cyclohexyl]-2-(4-hydroxy- 3,5-difluorophenyl)ethane (Example 1) is then added. The mixture is stirred at 150° for about 8 hors, cooled, poured into ice water, and the autoclave is subsequently washed out with ether. The two phases are combined, stirred for about 30 minutes, separated, and the ether solution is washed with 5% KOH solution until it remains alkaline. The organic phase is dried, filtered, evaporated, and the residue is purified to give 1-[trans-4-(trans-4-n-propylcyclohexyl)cyclohexyl]-2-(4-trifluoromethoxy- 3,5-difluorophenyl)ethane.

Examples 25 to 45

The following compounds are obtained analogously from the corresponding precursors of the formula II:

| | R | $(A^1-Z^1)_m-A^2-Z^2-$ | Q—Y | L |
|---|---|---|---|---|
| (25) | n-Butyl | Cy(H)—Cy(H)—CH₂CH₂— | OCF₃ | F |
| (26) | n-Pentyl | Cy(H)—Cy(H)—CH₂CH₂— | OCF₃ | F |
| (27) | n-Heptyl | Cy(H)—Cy(H)—CH₂CH₂— | OCF₃ | F |
| (28) | Ethyl | Ph—Ph—CH₂CH₂— | OCF₃ | F |
| (29) | Methoxy | Ph—Ph—CH₂CH₂— | OCF₃ | F |
| (30) | Ethoxy | Ph—Ph—CH₂CH₂— | OCF₃ | F |
| (31) | n-Propyl | Ph—Ph—CH₂CH₂— | OCF₃ | F |
| (32) | n-Pentyl | Ph—Ph—CH₂CH₂— | OCF₃ | F |
| (33) | Methoxymethyl | Ph—Ph—CH₂CH₂— | OCF₃ | F |
| (34) | n-Propyl | Ph—CH₂CH₂—Ph— | OCF₃ | F |
| (35) | n-Pentyl | Ph—CH₂CH₂—Ph— | OCF₃ | F |
| (36) | n-Propyl | Cy(H)—CH₂CH₂—Ph— | OCF₃ | F |
| (37) | n-Pentyl | Cy(H)—CH₂CH₂—Ph— | OCF₃ | F |
| (38) | n-Propyl | Cy(H)—Ph— | OCF₃ | F |
| (39) | n-Butyl | Cy(H)—Ph— | OCF₃ | F |
| (40) | n-Pentyl | Cy(H)—Ph— | OCF₃ | F |
| (41) | n-Propyl | Ph—Ph— | OCF₃ | F |
| (42) | n-Pentyl | Ph—Ph— | OCF₃ | F |
| (43) | n-Propyl | Cy(H)—Cy(H)— | OCF₃ | F |
| (44) | n-Butyl | Cy(H)—Cy(H)— | OCF₃ | F |
| (45) | n-Pentyl | Cy(H)—Cy(H)— | OCF₃ | F |

Example 46

31.6 g of 2-fluoro-4-[trans-4-(trans-4-n-propylcyclohexyl)cyclohexyl] phenol (prepared by hydrogenation from the corresponding benzyl ether, which had been obtained by cross-coupling of bis[trans-4-(trans-4-n-propylcyclohexyl- )cyclohexyl] zinc with 4-bromo-2-fluorobenzyl phenyl ether) and 49.3 g of carbon tetrachloride are initially introduced into a Hatelloy autoclave and cooled with dry ice/acetone.

After the autoclave has been evacuated, 66.7 g of HF and 1.67 g of $BF_3$ are added. After stirring at 150° C. for 8 hours, the mixture is allowed to cool to room temperature, and the HF is removed by means of an aspirator. The residue is taken up in methylene chloride, and NaF is added to separate off any remaining HF. The mixture is filtered, the filtrate is evaporated, the residue is purified by chromatography over silica gel and repeated crystallization from hexane and ethanol to give 2-fluoro- 4-[trans-4-(trans-4-n-propylcyclohexyl)cyclohexyl]trifluoromethoxybenzene.

Examples 47 to 68

The following compounds are obtained analogously from the corresponding phenols:

|      | R | $(A^1-Z^1)_m-A^2-Z^2-$ | Q—Y | L |
|------|---|---|---|---|
| (47) | n-Propyl | —(H)—(H)—CH₂CH₂— | $OCF_3$ | H |
| (48) | n-Pentyl | —(H)—(H)—CH₂CH₂— | $OCF_3$ | H |
| (49) | n-Heptyl | —(H)—(H)—CH₂CH₂— | $OCF_3$ | H |
| (50) | Ethyl | —(O)—(O)—CH₂CH₂— | $OCF_3$ | H |
| (51) | Methoxy | —(O)—(O)—CH₂CH₂— | $OCF_3$ | H |
| (52) | Ethoxy | —(O)—(O)—CH₂CH₂— | $OCF_3$ | H |
| (53) | n-Propyl | —(O)—(O)—CH₂CH₂— | $OCF_3$ | H |
| (54) | n-Pentyl | —(O)—(O)—CH₂CH₂— | $OCF_3$ | H |
| (55) | Methoxymethyl | —(O)—(O)—CH₂CH₂— | $OCF_3$ | H |
| (56) | n-Propyl | —(O)—CH₂CH₂—(O)— | $OCF_3$ | H |
| (57) | n-Pentyl | —(O)—CH₂CH₂—(O)— | $OCF_3$ | H |
| (58) | n-Propyl | —(H)—CH₂CH₂—(O)— | $OCF_3$ | H |
| (59) | n-Pentyl | —(H)—CH₂CH₂—(O)— | $OCF_3$ | H |
| (60) | n-Propyl | —(H)—(O)— | $OCF_3$ | H |
| (61) | n-Butyl | —(H)—(O)— | $OCF_3$ | H |
| (62) | n-Pentyl | —(H)—(O)— | $OCF_3$ | H |
| (63) | n-Propyl | —(O)—(O)— | $OCF_3$ | H |
| (64) | n-Pentyl | —(O)—(O)— | $OCF_3$ | H |
| (65) | Ethyl | —(H)—(H)— | $OCF_3$ | H |
| (66) | n-Propyl | —(H)—(H)— | $OCF_3$ | H |
| (67) | n-Butyl | —(H)—(H)— | $OCF_3$ | H |
| (68) | n-Pentyl | —(H)—(H)— | $OCF_3$ | H |

Examples 69 to 91

The following compounds are obtained analogously to Example 1 from the corresponding phenols:

|      | R | $(A^1-Z^1)_m-A^2-Z^2-$ | Q—Y | L |
|------|---|---|---|---|
| (69) | Ethyl | —(H)—(H)—CH₂CH₂— | $OCHF_2$ | H |
| (70) | n-Butyl | —(H)—(H)—CH₂CH₂— | $OCHF_2$ | H |
| (71) | n-Pentyl | —(H)—(H)—CH₂CH₂— | $OCHF_2$ | H |
| (72) | n-Heptyl | —(H)—(H)—CH₂CH₂— | $OCHF_2$ | H |

-continued
| R | (A¹−Z¹)ₘ−A²−Z²− | Q−Y | L |
|---|---|---|---|
| (73) Ethyl | 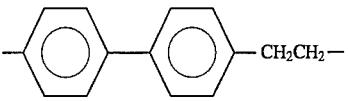 | OCHF₂ | H |
| (74) Methoxy | 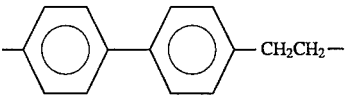 | OCHF₂ | H |
| (75) Ethoxy | 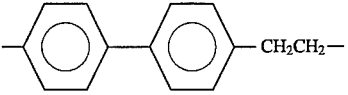 | OCHF₂ | H |
| (76) n-Propyl |  | OCHF₂ | H |
| (77) n-Pentyl | 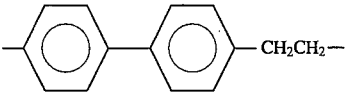 | OCHF₂ | H |
| (78) Methoxymethyl | 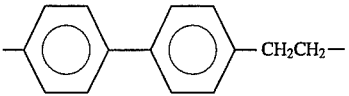 | OCHF₂ | H |
| (79) n-Propyl | 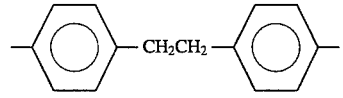 | OCHF₂ | H |
| (80) n-Pentyl | 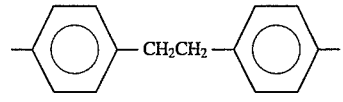 | OCHF₂ | H |
| (81) n-Propyl | 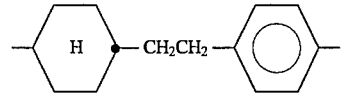 | OCHF₂ | H |
| (82) n-Pentyl | 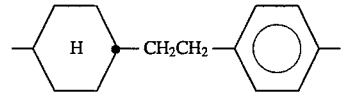 | OCHF₂ | H |
| (83) n-Propyl | 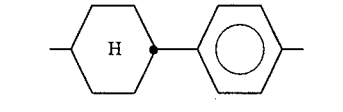 | OCHF₂ | H, C50N121I |
| (84) n-Butyl | 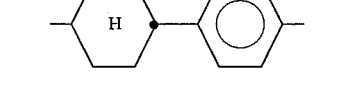 | OCHF₂ | H |
| (85) n-Pentyl | 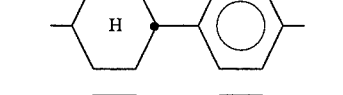 | OCHF₂ | H, C38N123I |
| (86) n-Propyl | 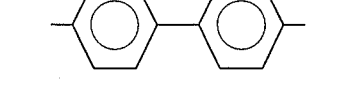 | OCHF₂ | H |

| R | $(A^1-Z^1)_m-A^2-Z^2-$ | Q—Y | L |
|---|---|---|---|
| (87) n-Pentyl | 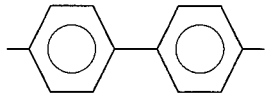 | OCHF$_2$ | H |
| (88) Ethyl |  | OCHF$_2$ | H, C15N108I |
| (89) n-Propyl | 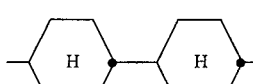 | OCHF$_2$ | H, C33N144I |
| (90) n-Butyl | 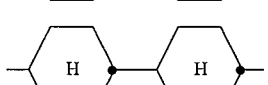 | OCHF$_2$ | H, C37N143I |
| (91) n-Pentyl | 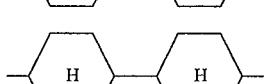 | OCHF$_2$ | H, C37S$_B$(21) N149I |
| (92) Ethyl | 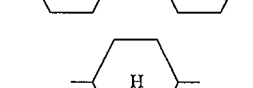 | OCHF$_2$ | H |
| (93) n-Propyl | 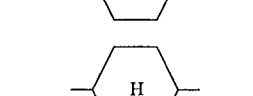 | OCHF$_2$ | H |
| (94) n-Butyl | 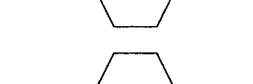 | OCHF$_2$ | H |
| (95) n-Pentyl | 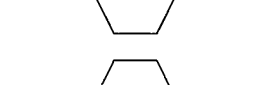 | OCHF$_2$ | H, C9I |
| (96) n-Heptyl | 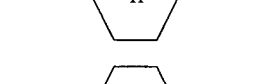 | OCHF$_2$ | H. C7N(−28) I |
| (97) n-Propyl | 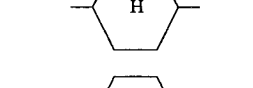 | OCHF$_2$ | H |
| (98) n-Pentyl |  | OCHF$_2$ | H |

Example 99

0.1 mol of n-BuLi (1.5M in hexane) is added dropwise at about −65° to a solution of 0.1 mol of 1-[trans-4-(trans-4-n-propylcyclohexyl)cyclohexyl]-2-(3,5-difluorophenyl)ethane (prepared according to scheme 3) and 0.1 mol of TMEDA in 300 ml of THF. Stirring at this temperature is continued for another 30 minutes, and 0.2 mol of N-chlorosuccinimide in 70 ml of THF are then slowly added. After the addition is completed, the mixture is allowed to warm to −20° and hydrolyzed with H$_2$O. Diethyl ether is added until the product is completely dissolved. Extractive work-up and purification by chromatography and crystallization gives 1-[trans-4-(trans-4-n-propylcyclohexyl)cyclohexyl]- 2-(4-chloro-3,5-difluorophenyl)ethane, C 88 N 129 I.

Examples 100 to 143

The following compounds according to the invention are obtained analogously from the corresponding precursors of the formula II:

| R | $(A^1-Z^1)_m-A^2-Z^2-$ | Q—Y |
|---|---|---|
| (100) Ethyl | —Cy—Cy—CH$_2$CH$_2$— | Cl |
| (101) n-Butyl | —Cy—Cy—CH$_2$CH$_2$— | Cl |
| (102) n-Pentyl | —Cy—Cy—CH$_2$CH$_2$— | Cl |
| (103) n-Heptyl | —Cy—Cy—CH$_2$CH$_2$— | Cl |
| (104) Ethyl | —Ph—Ph—CH$_2$CH$_2$— | Cl |
| (105) Methoxy | —Ph—Ph—CH$_2$CH$_2$— | Cl |
| (106) Ethoxy | —Ph—Ph—CH$_2$CH$_2$— | Cl |
| (107) n-Propyl | —Ph—Ph—CH$_2$CH$_2$— | Cl |
| (108) n-Pentyl | —Ph—Ph—CH$_2$CH$_2$— | Cl |
| (109) Methoxymethyl | —Ph—Ph—CH$_2$CH$_2$— | Cl |
| (110) n-Propyl | —Ph—CH$_2$CH$_2$—Ph— | Cl |
| (111) n-Pentyl | —Ph—CH$_2$CH$_2$—Ph— | Cl |
| (112) n-Propyl | —Cy—CH$_2$CH$_2$—Ph— | Cl |
| (113) n-Pentyl | —Cy—CH$_2$CH$_2$—Ph— | Cl |
| (114) n-Propyl | —Cy—Ph— | Cl |
| (115) n-Butyl | —Cy—Ph— | Cl |
| (116) n-Pentyl | —Cy—Ph— | Cl |
| (117) n-Propyl | —Ph—Ph— | Cl |
| (118) n-Pentyl | —Ph—Ph— | Cl |
| (119) n-Propyl | —Cy—Cy— | Cl |
| (120) n-Butyl | —Cy—Cy— | Cl |
| (121) n-Pentyl | —Cy—Cy— | Cl |
| (122) Ethyl | —Cy—Cy—CH$_2$CH$_2$— | F |
| (123) n-Butyl | —Cy—Cy—CH$_2$CH$_2$— | F |
| (124) n-Pentyl | —Cy—Cy—CH$_2$CH$_2$— | F |
| (125) n-Heptyl | —Cy—Cy—CH$_2$CH$_2$— | F |
| (126) Ethyl | —Ph—Ph—CH$_2$CH$_2$— | F |
| (127) Methoxy | —Ph—Ph—CH$_2$CH$_2$— | F |
| (128) Ethoxy | —Ph—Ph—CH$_2$CH$_2$— | F |
| (129) n-Propyl | —Ph—Ph—CH$_2$CH$_2$— | F |
| (130) n-Pentyl | —Ph—Ph—CH$_2$CH$_2$— | F |
| (131) Methoxymethyl | —Ph—Ph—CH$_2$CH$_2$— | F |
| (132) n-Propyl | —Ph—CH$_2$CH$_2$—Ph— | F |
| (133) n-Pentyl | —Ph—CH$_2$CH$_2$—Ph— | F |
| (134) n-Propyl | —Cy—CH$_2$CH$_2$—Ph— | F |
| (135) n-Pentyl | —Cy—CH$_2$CH$_2$—Ph— | F |
| (136) n-Propyl | —Cy—Ph— | F, C42N (33) I |
| (137) n-Butyl | —Cy—Ph— | F |
| (138) n-Pentyl | —Cy—Ph— | F, C20 N42I |
| (139) n-Propyl | —Ph—Ph— | F |
| (140) n-Pentyl | —Ph—Ph— | F |
| (141) n-Propyl | —Cy—Cy— | F, C64 N78I |
| (142) n-Butyl | —Cy—Cy— | F |
| (143) n-Pentyl | —Cy—Cy— | F, C86 N91I |

Example 144

A mixture of 0.1 mol of 4-(trans-4-n-phenylcyclohexyl)-2-fluorobenzoic acid and 0.3 mol of SF$_4$ is heated in an autoclave at 130° for 8 hours. The crude product obtained is taken up in pentane and subjected to extractive work-up. Conventional purification by distillation and crystallization gives 4-(trans-4-n-pentylcyclohexyl)-2-fluorobenzo trifluoride.

Example 145

0.01 mol of TMEDA is added to a solution of 0.01 mol of 4-(trans-4-n-propylcyclohexyl)-4'-trifluoromethylbiphenyl in 10 ml of n-hexane. At 0°–5° C. 0.01 mol of n-BuLi is added, and stirring at RT is continued for another half an hour and at 40° C. for half an hour. The mixture is then cooled to 0° C., 20 ml of THF are added, and the fluorinating agent 1-fluoro-2,4,6-trimethylpyridinium triflate (in THF) is added dropwise at this temperature according to scheme 21. Extractive work-up and, as is customary, chromatography and crystallization give 4-(trans-4-n-propylcyclohexyl)-3'-fluoro-4'-trifluoromethylbiphenyl.

Examples 146 to 175

The following compounds are obtained from the corresponding precursors analogously to Examples 144 or 145:

| R | $(A^1-Z^1)_m-A^2-Z^2-$ | Q—Y | L |
|---|---|---|---|
| (146) Ethyl | Cy(H)–Cy(H)–CH$_2$CH$_2$– | CF$_3$ | H |
| (147) n-Butyl | Cy(H)–Cy(H)–CH$_2$CH$_2$– | CF$_3$ | H |
| (148) n-Pentyl | Cy(H)–Cy(H)–CH$_2$CH$_2$– | CF$_3$ | H |
| (149) n-Heptyl | Cy(H)–Cy(H)–CH$_2$CH$_2$– | CF$_3$ | H |
| (150) Ethyl | Ph–Ph–CH$_2$CH$_2$– | CF$_3$ | H |
| (151) Methoxy | Ph–Ph–CH$_2$CH$_2$– | CF$_3$ | H |
| (152) Ethoxy | Ph–Ph–CH$_2$CH$_2$– | CF$_3$ | H |
| (153) n-Propyl | Ph–Ph–CH$_2$CH$_2$– | CF$_3$ | H |
| (154) n-Pentyl | Ph–Ph–CH$_2$CH$_2$– | CF$_3$ | H |
| (155) Methoxymethyl | Ph–Ph–CH$_2$CH$_2$– | CF$_3$ | H |
| (156) n-Propyl | Ph–CH$_2$CH$_2$–Cy– | CF$_3$ | H |
| (157) n-Pentyl | Ph–CH$_2$CH$_2$–Cy– | CF$_3$ | H |

| R | $(A^1-Z^1)_m-A^2-Z^2-$ | Q—Y | L |
|---|---|---|---|
| (158) n-Propyl | 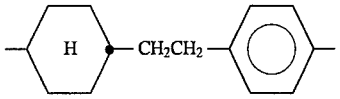 | CF₃ | H |
| (159) n-Pentyl | 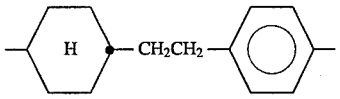 | CF₃ | H |
| (160) n-Propyl | 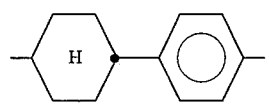 | CF₃ | H |
| (161) n-Butyl | 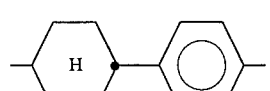 | CF₃ | H |
| (162) n-Pentyl | 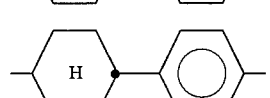 | CF₃ | H |
| (163) n-Propyl | 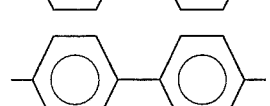 | CF₃ | H |
| (164) n-Pentyl |  | CF₃ | H |
| (165) Ethyl |  | CF₃ | H |
| (166) n-Propyl |  | CF₃ | H, C115I $\Delta\epsilon = +10{,}2$ |
| (167) n-Butyl |  | CF₃ | H |
| (168) n-Pentyl |  | CF₃ | H |
| (169) Ethyl | 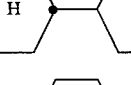 | CF₃ | H |
| (170) n-Propyl | 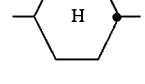 | CF₃ | H |
| (171) n-Butyl | 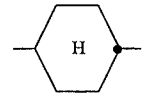 | CF₃ | H |
| (172) n-Pentyl | 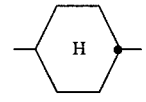 | CF₃ | H |

-continued

| R | $(A^1-Z^1)_m-A^2-Z^2-$ | Q—Y | L |
|---|---|---|---|
| (173) n-Heptyl | 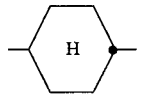 | CF$_3$ | H |
| (174) n-Propyl | 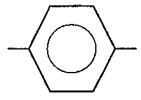 | CF$_3$ | H |
| (175) n-Pentyl | 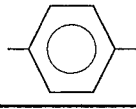 | CF$_3$ | H |

Example 176

A mixture of 0.025 mol of CuI, 0.0125 mol of CF$_3$COONa and 0.0125 mol of 1-[trans-4-(trans-4-n-propylcyclohexyl)cyclohexyl] -2-(4-iodo-3,5-difluorophenyl)ethane [obtainable according to scheme 15] is heated in 100 ml of N-methylpyrrolidone to 150° with stirring. After one hour, the mixture is subjected as usual to extractive work-up to give, after purification by chromatography, 1-[trans-4-(trans-4-n-propylcyclohexyl)cyclohexyl]-2-(4-trifluoromethyl- 3,5-difluorophenyl)ethane.

Examples 177 to 206

The following compounds are obtained from the corresponding 3,5-difluorophenyl compounds analogously to Example 176:

| R | $(A^1-Z^1)_m-A^2-Z^2-$ | Q—Y | L |
|---|---|---|---|
| (177) Ethyl | 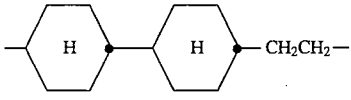 | CF$_3$ | F |
| (178) n-Butyl | 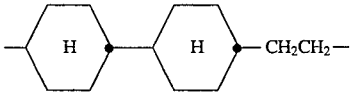 | CF$_3$ | F |
| (179) n-Pentyl | 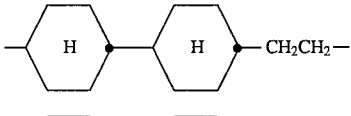 | CF$_3$ | F |
| (180) n-Heptyl | 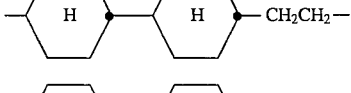 | CF$_3$ | F |
| (181) Ethyl | 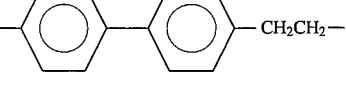 | CF$_3$ | F |
| (182) Methoxy |  | CF$_3$ | F |
| (183) Ethoxy | 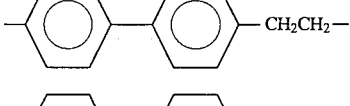 | CF$_3$ | F |
| (184) n-Propyl | 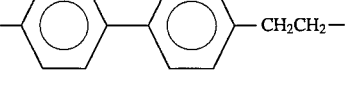 | CF$_3$ | F |

-continued
| R | $(A^1-Z^1)_m-A^2-Z^2-$ | Q—Y | L | |
|---|---|---|---|---|
| (185) n-Pentyl | 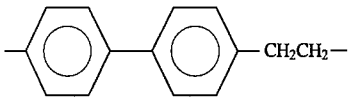 | CF₃ | F | |
| (186) Methoxymethyl | 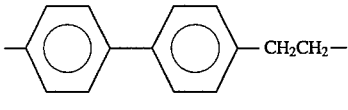 | CF₃ | F | |
| (187) n-Propyl | 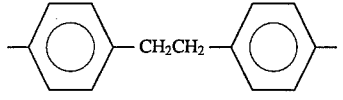 | CF₃ | F | |
| (188) n-Pentyl | 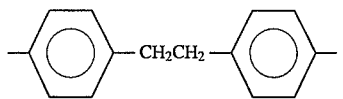 | CF₃ | F | |
| (189) n-Propyl | 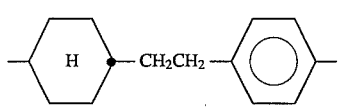 | CF₃ | F | |
| (190) n-Pentyl | 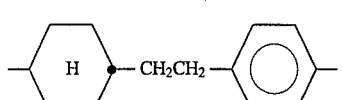 | CF₃ | F | |
| (191) n-Propyl | 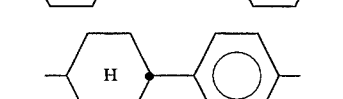 | CF₃ | F | |
| (192) n-Butyl | 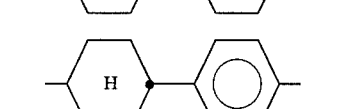 | CF₃ | F | |
| (193) n-Pentyl | 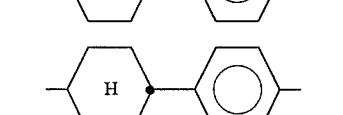 | CF₃ | F | |
| (194) n-Propyl |  | CF₃ | F | |
| (195) n-Pentyl |  | CF₃ | F | |
| (196) Ethyl |  | CF₃ | F | |
| (197) n-Propyl | 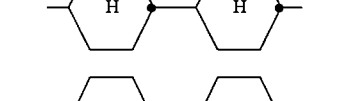 | CF₃ | F, | C93I $\Delta\epsilon = +13,1$ |
| (198) n-Butyl | 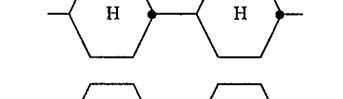 | CF₃ | F | |
| (199) n-Pentyl | 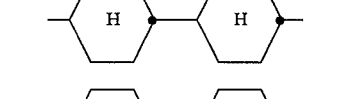 | CF₃ | F | |

-continued

| R | $(A^1-Z^1)_m-A^2-Z^2-$ | Q—Y | L |
|---|---|---|---|
| (200) Ethyl | 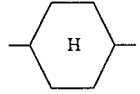 | $CF_3$ | F |
| (201) n-Propyl | 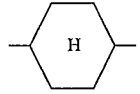 | $CF_3$ | F |
| (202) n-Butyl | 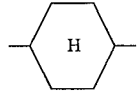 | $CF_3$ | F |
| (203) n-Pentyl | 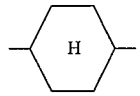 | $CF_3$ | F |
| (204) n-Heptyl | 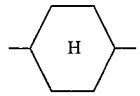 | $CF_3$ | F |
| (205) n-Propyl | 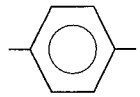 | $CF_3$ | F |
| (206) n-Pentyl | 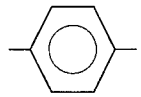 | $CF_3$ | F |

Example 207

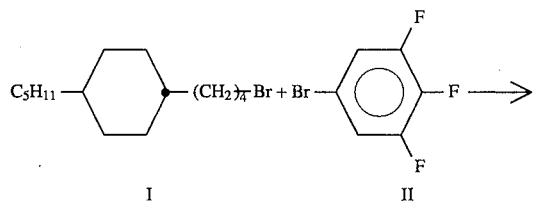

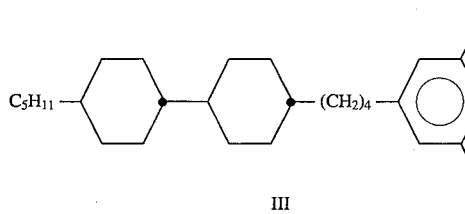

37.1 g of I (0.1 mol) are initially introduced into 150 ml of a solvent mixture of THF/toluene (1:4 volume ratio), then 11.5 g of anhydrous zinc bromide and, after that, 1.4 g of lithium granules are added. The mixture is treated between 0° C. and 10° C. with ultrasound under argon and with stirring for 4 hours in order to convert I into the corresponding dialkyl zinc compound. 21.1 g of II (0.1 mol) and 1.5 g (2 mol %) of 1,1'-bis(diphenylphosphino)ferrocene-palladium(II) dichloride ($PdCl_2$dppt) are added to the organozinc compound and, after removal of the ultrasonic bath and the cooling, stirred at room temperature for 24 h. The mixture is decomposed with 100 ml of saturated $NH_4Cl$ solution with stirring, the organic phase is separated off, and the aqueous phase is extracted twice with toluene. The combined organic extracts give III after drying, concentrating and chromatographing on silica gel with hexane. (I can be prepared by chain elongation of

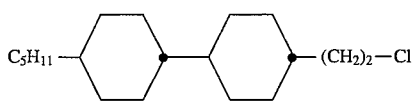

by means of malonic ester). The alkyl bromides listed below can be reacted with II analogously to I:

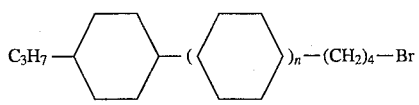

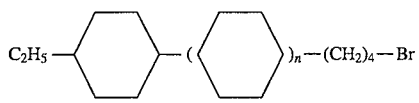

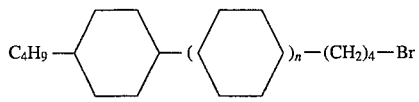

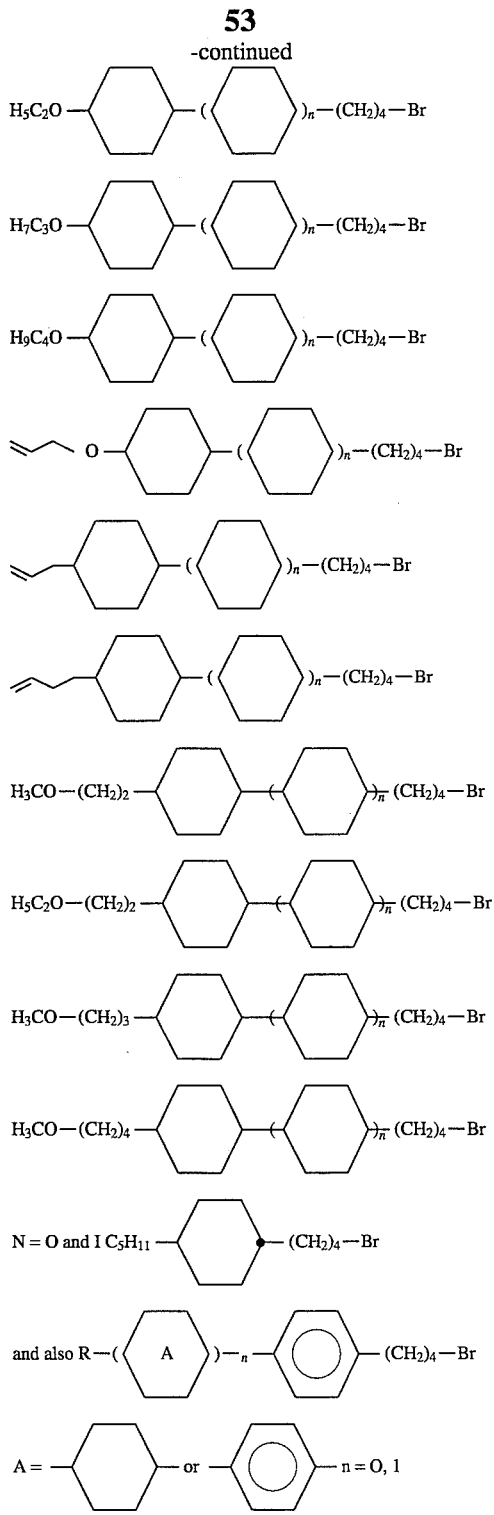

Example 208

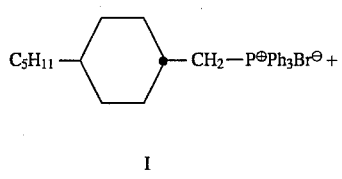

I

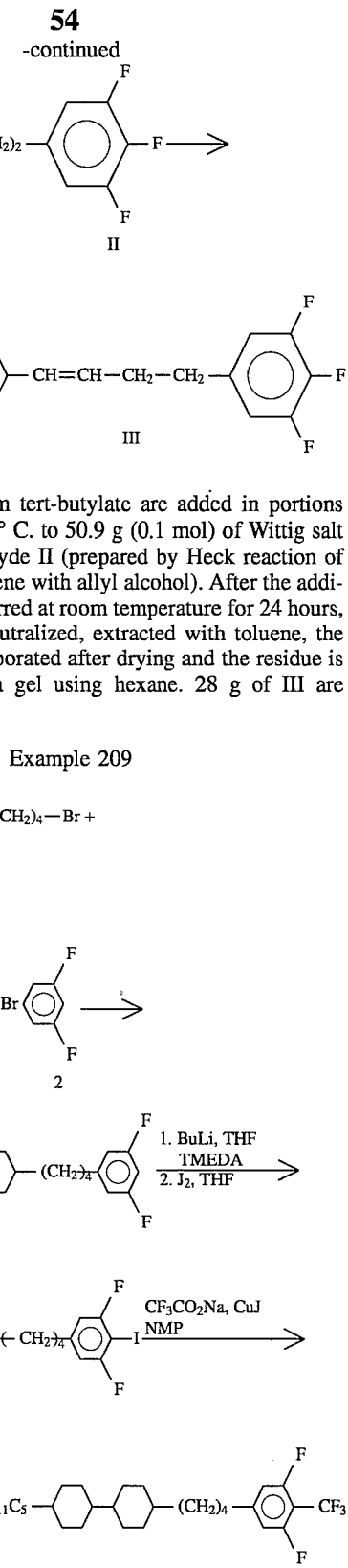

11.5 g of potassium tert-butylate are added in portions between 0° C. and 10° C. to 50.9 g (0.1 mol) of Wittig salt I and 17.2 g of aldehyde II (prepared by Heck reaction of 1-bromotrifluorobenzene with allyl alcohol). After the addition, the mixture is stirred at room temperature for 24 hours, poured into water, neutralized, extracted with toluene, the toluene extract is evaporated after drying and the residue is filtered through silica gel using hexane. 28 g of III are obtained.

Example 209

37.1 g (100 mmol) of 1 are converted into 3 by reaction with 2 analogously to Example 207.

31 ml of n-Buli (sic) (15% in hexane) are added dropwise at −65° to −70° C. to a mixture of 19.0 g (47 mmol) of 3, 7.5 ml of TMEDA (50 mmol) and 150 ml of THF and the mixture is subsequently stirred at −70° C. for 1 hour. A solution of 12.0 g (47 mmol) of iodine in 25 ml of THF is then added dropwise at −65° to −70° C. and the mixture is subsequently stirred at −70° C. for 0.5 h. It is warmed to −30° C., hydrolyzed with 15 ml of water and excess iodine is reduced by addition of 15 ml of sodium hydrogensulphite solution. Customary work-up and recrystallization from hexane gives 23.9 g (45 mmol) of 4. 400 ml of NMP are removed by distillation at 70° C. and 4 mbar from a mixture of 20.2 g (38 mmol) of 4, 4.4 g (76 mmol) of KF, 22.8 g (168 mmol) of sodium trifluoroacetate and 800 ml of NMP. 14.4 g (76 mmol) of dried CuI are then added to the reaction mixture and it is stirred at 160° C. for 5 h. About 300 ml of NMP are then removed by distillation. The mixture is allowed to cool to RT and 300 ml of MTB ether are added. The mixture is washed with water, dried using Na$_2$SO$_4$, filtered and concentrated to give a residue. Chromatography on silica gel using hexane gives 5.

Example 210

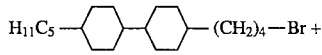

1

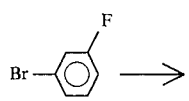

11

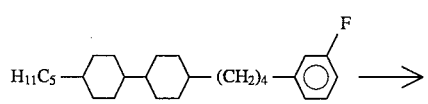

12

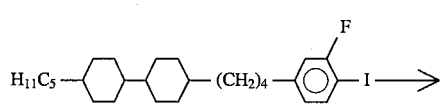

13

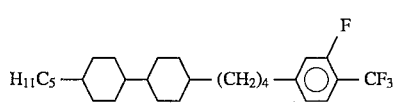

14

31.1 g (100 mmol) of 1 are converted into 12 by reaction with 11 analogously to Example 207.

40 ml of n-BuLi are added dropwise at −100° C. to a mixture of 18.2 g (47 mmol) of 12, 7.4 g of potassium tertiary butylate and 110 ml of THF and the mixture is subsequently stirred at −100° C. for 1 h. A solution of 15.9 g of iodine in 60 ml of THF is then added dropwise at −85° to −90° C. The mixture is subsequently stirred at −90° C. for a further 0.5 h, warmed to −30° C., hydrolyzed with 30 ml of water and acidified with conc. hydrochloric acid, and excess iodine is reduced by addition of sodium hydrogensulphite solution. Customary working-up and recrystallization from hexane gives 21.4 g (41 mmol) of 13. 19.5 g (38 mmol) of 13 are converted into 14 by conversion with sodium trifluoroacetate according to Example 209. Chromatographic purification gives 14.

Example 211

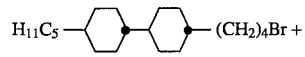

1

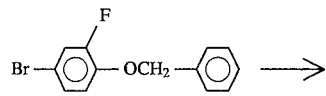

2

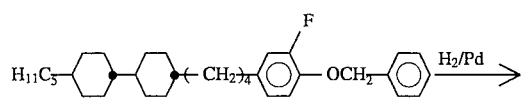

3

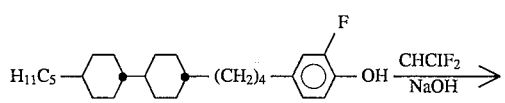

4

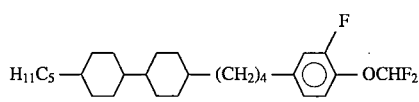

5

According to the above synthesis scheme, the compound 3 is obtained analogously to Example 207 after conversion of 1 into the organozinc compound by a Pd(II)-catalyzed coupling reaction with 2. Hydrogenolytic cleavage of the benzyl ether leads to the phenol 4.

4.0 g (0.01 mol) of this phenol are initially introduced into THF, 3.1 g of 32% sodium hydroxide solution and 0.5 g of tetrabutylammonium hydrogensulphate are added, the mixture is warmed to 50° C. and chlorodifluoromethane is introduced with stirring until it condenses in a condenser cooled with dry ice. After cooling, the THF solution is decanted off from the precipitated oily product and concentrated, and the 5 obtained is recrystallized from ethanol.

Example 212

25 ml of butyllithium (15% in hexane) are added dropwise at −70° C. to a solution of 15 g of 4-(trans-4-n-propylcyclohexyl)- 2-fluoro-4'-bromobiphenyl in 50 ml of THF and a cooled solution of 4.5 g of ZnBr$_2$ in 25 ml of THF is added after 30 min. After addition of 8.5 g of 1-bromo-3,4,5-trifluorobenzene in 75 ml of THF and 0.6 g of PdCl$_2$-dppf, the mixture is allowed to come to room temperature. After stirring for 24 h, the mixture is poured into 100 ml of saturated NH$_4$Cl solution and worked up as usual. 4"-(trans-4-n-Propylcyclohexyl)-2",3,4,5-tetrafluoroterphenyl is obtained, C 148 N 233 I.

The following are obtained analogously from the corresponding bromoaromatics:

4"-n-Propyl-2",3,4,5-tetrafluoroterphenyl

4"-n-Pentyl-2",3,4,5-tetrafluoroterphenyl

4'-(trans-4-Methoxymethylcyclohexyl)-3,4,5-trifluorobiphenyl

Example 213

A mixture of 10.5 g of 1-bromo-3,4,5-trifluorobenzene, 7.4 g of p-ethoxystyrene, 0.25 g of Pd acetate, 0.6 g of tri-o-tolylphosphine, 7 g of triethylamine and 125 ml of acetonitrile is heated at reflux until completion of the reaction. Customary working-up gives 1-(p-ethoxyphenyl)-2-(3,4,5-trifluorophenyl)ethene (C 76 I), which is hydrogenated on PD-C (5%) in THF to give 1-(p-ethoxyphenyl)-2-(3,4,5-trifluorophenyl)ethane, C 45 I.

Example 214

1-(p-Ethoxyphenyl)-2-(3-fluoro-4-benzyloxyphenyl)ethene is obtained from p-ethoxystyrene and the benzyl ether of p-bromo-o-fluorophenol analogously to Example 213. Hydrogenation on Pd-C (5%) in THF gives 1-(p-ethoxyphenyl)- 2-(4-hydroxy-3-fluorophenyl)ethane, of which 41.3 g together with 5.6 g of tetrabutylammonium hydrogensulphate are dissolved in 500 ml of THF at 40° C. 43 g of chlorodifluoromethane are introduced into this solution in such a way that a small amount condenses in the dry ice reflux condenser. 32 g of NaOH (50%) are then added dropwise with vigorous stirring in the course of 10 min. After stirring at 40° for a further hour, the mixture is cooled and decanted off from the oily precipitate formed. After evaporating the solvent, the residue is purified by chromatography and recrystallization. 1-(p-Ethoxyphenyl)-2-(3-fluoro-4-difluoromethoxyphenyl)ethane is obtained, C 43 I.

Example 215

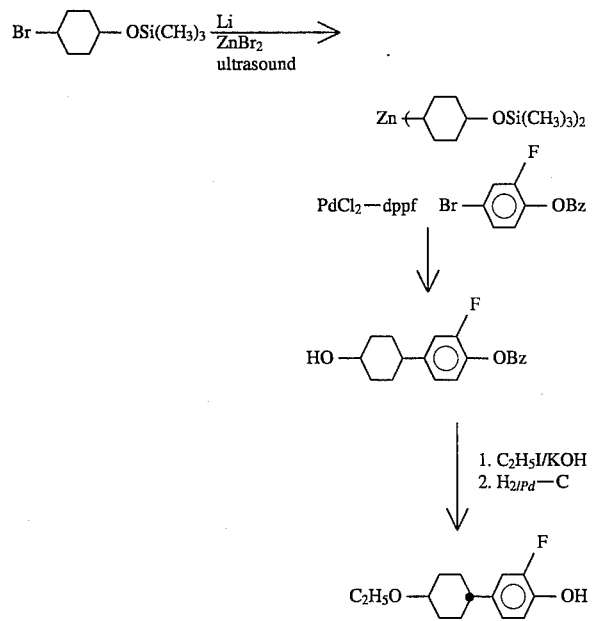

11 g of NaOH (32%) are added to a solution of 8.2 (lacuna) of the resultant p-(trans-4-ethoxycyclohexyl)-o-fluorophenol in 80 ml of THF and 13.8 g of chlorodifluoromethane are introduced (dry ice reflux condenser). After subsequently stirring for one hour, the solution is decanted off from the precipitate and concentrated to give a residue. Bulb tube distillation gives p-(trans-4-ethoxycyclohexyl)-o-fluorodifluoromethoxybenzene, b.p.$_1$~220° C., Tg −62°.

Example 216

2-n-Octyloxy-5-(3-fluoro-4-hydroxyphenyl)pyridine [prepared by reaction of 2,5-dibromopyridine with NaH/1-octanol, conversion of the 2-n-octyloxy-5-bromopyridine into the zinc compound (BuLi/ZnBr$_2$/−70°), cross-coupling with 3-fluoro-4-acetoxybromobenzene (PdCl$_2$dppf/THF) and hydrolysis of the acetyl group with KOH/MeOH] gives 2-n-octyloxy-5-(3-fluoro-4-difluoromethoxyphenyl)pyridine, C 29 I, analogously to Example 214.

The following are prepared analogously:

2-n-Octyl-5-(3-fluoro-4-difluoromethoxyphenyl)pyridine, C 29 I.

Example A

| PCH-5F | 10.0% | S→N [°C.] | <−40 |
|---|---|---|---|
| PCH-6F | 7.0% | Clear point [°C.] | +64 |
| PCH-7F | 15.0% | Viscosity 20° C. | 14 |
| CCP-20CF$_3$ | 10.0% | Δn (589 nm, 20° C.) | 0.0800 |
| CCP-30CF$_3$ | 12.0% | n$_e$ (589 nm, 20° C.) | 1.5576 |
| CCP-40CF$_3$ | 8.0% | V$_{(10,0,20)}$ | 1.61 |
| CCP-50CF$_3$ | 12.0% | V$_{(50,0,20)}$ | 2.04 |
| CCp-3F.F.F | 10.0% | V$_{(90,0,20)}$ | 2.66 |
| BCH-5F.F | 16.0% | | |

Example B

| PCH-5F | 12.0% | S→N [°C.] | <−30 |
|---|---|---|---|
| PCH-7F | 8.0% | Clear point [°C.] | +80 |
| CCP-20CF$_3$ | 10.0% | Viscosity 20° C. | — |
| CCP-30CF$_3$ | 12.0% | Δn (589 nm, 20° C.) | +0.0756 |
| CCP-40CF$_3$ | 8.0% | n$_e$ (589 nm, 20° C.) | 1.5489 |
| CCP-50CF$_3$ | 12.0% | V$_{(10,0,20)}$ | 1.66 |
| ECP-3F.F | 12.0% | V$_{(50,0,20)}$ | 2.12 |
| CCP-3F.F.F | 14.0% | V$_{(90,0,20)}$ | 2.73 |
| CCP-5F.F.F | 12.0% | | |

Example C

| PCH-5F | 12.0% | S→N [°C.] | — |
|---|---|---|---|
| PCH-7F | 7.0% | Clear point [°C.] | +78 |
| CCP-20CF$_3$ | 10.0% | Viscosity 20° C. | 16 |
| CCP-30CF$_3$ | 12.0% | Δn (589 nm, 20° C.) | 0.0844 |
| CCP-40CF$_3$ | 8.0% | n$_e$ (589 nm, 20° C.) | 1.5610 |
| CCP-50CF$_3$ | 12.0% | V$_{(10,0,20)}$ | 1.61 |
| BCP-3F.F | 8.0% | V$_{(50,0,20)}$ | 2.06 |
| BCH-5F.F | 6.0% | V$_{(90,0,20)}$ | 2.72 |
| CCP-3F.F.F | 16.0% | | |
| CCP-5F.F.F | 12.0% | | |

Example D

| PCH-5F | 12.0% | S→N [°C.] | — |
|---|---|---|---|
| PCH-7F | 8.0% | Clear point [°C.] | +77 |
| CCP-20CF$_3$ | 10.0% | Viscosity 20° C. | — |
| CCP-30CF$_3$ | 12.0% | Δn (589 nm, 20° C.) | +0.0847 |
| CCP-40CF$_3$ | 8.0% | n$_e$ (589 nm, 20° C.) | 1.5605 |
| CCP-50CF$_3$ | 12.0% | V$_{(10,0,20)}$ | 1.59 |
| BCP-3F.F.F | 14.0% | V$_{(50,0,20)}$ | — |
| ECCP-3F.F | 12.0% | V$_{(90,0,20)}$ | — |
| CCP-5F.F.F | 12.0% | | |

Example E

| | | | |
|---|---|---|---|
| PCH-5F | 11.0% | S→N [°C.] | — |
| PCH-7F | 9.0% | Clear point [°C.] | +75 |
| CCP-20CF$_3$ | 8.0% | Viscosity 20° C. | — |
| CCP-30CF$_3$ | 10.0% | Δn (589 nm, 20° C.) | +0.0876 |
| CCP-40CF$_3$ | 7.0% | $n_e$ (589 nm, 20° C.) | 1.5666 |
| CCP-50CF$_3$ | 10.0% | $V_{(10,0,20)}$ | 1.51 |
| BCP-3F.F | 10.0% | $V_{(50,0,20)}$ | 1.95 |
| BCH-5F.F | 10.0% | $V_{(90,0,20)}$ | 2.54 |
| CCP-3F.F.F | 13.0% | | |
| CCP-5F.F.F | 13.0% | | |

Example F

| | | | |
|---|---|---|---|
| PCH-5F | 12.0% | S→N [°C.] | — |
| PCH-7F | 7.0% | Clear point [°C.] | +76 |
| CCP-20CF$_3$ | 10.0% | Viscosity 20° C. | — |
| CCP-30CF$_3$ | 12.0% | Δn (589 nm, 20° C.) | 0.0835 |
| CCP-40CF$_3$ | 8.0% | $n_e$ (589 nm, 20° C.) | 1.5595 |
| CCP-50CF$_3$ | 12.0% | $V_{(10,0,20)}$ | 1.49 |
| BCH-3F.F.F | 8.0% | $V_{(50,0,20)}$ | 1.93 |
| BCH-5F.F | 6.0% | $V_{(90,0,20)}$ | 2.52 |
| CCP-3F.F.F | 16.0% | | |
| CCP-5F.F.F | 12.0% | | |

Example G

| | | | |
|---|---|---|---|
| PCH-5F | 8.0% | S→N [°C.] | — |
| PCH-7F | 4.0% | Clear point [°C.] | +81 |
| CCP-20CF$_3$ | 10.0% | Viscosity 20° C. | — |
| CCP-30CF$_3$ | 12.0% | Δn (589 nm, 20° C.) | +0.0907 |
| CCP-40CF$_3$ | 8.0% | $n_e$ (589 nm, 20° C.) | 1.5672 |
| CCP-50CF$_3$ | 12.0% | $V_{(10,0,20)}$ | 1.46 |
| BCH-3F.F.F | 14.0% | $V_{(50,0,20)}$ | — |
| BCH-5F.F.F | 10.0% | $V_{(90,0,20)}$ | — |
| CCP-3F.F.F | 10.0% | | |
| CCP-5F.F.F | 8.0% | | |
| ECCP-3F.F | 4.0% | | |

Example H

| | | | |
|---|---|---|---|
| PCH-5F | 8.0% | S→N [°C.] | — |
| CCP-20CF$_3$ | 10.0% | Clear point [°C.] | +86 |
| CCP-30CF$_3$ | 12.0% | Viscosity 20° C. | — |
| CCP-40CF$_3$ | 8.0% | Δn (589 nm, 20° C.) | +0.0930 |
| CCP-50CF$_3$ | 12.0% | $n_e$ (589 nm, 20° C.) | 1.5697 |
| BCH-3F.F.F | 14.0% | $V_{(10,0,20)}$ | 1.45 |
| BCH-5F.F.F | 11.0% | $V_{(50,0,20)}$ | 1.89 |
| CCP-3F.F.F | 12.0% | $V_{(90,0,20)}$ | 2.46 |
| CCP-5F.F.F | 7.0% | | |
| ECCP-3F.F | 6.0% | | |

We claim:

1. A liquid-crystals medium comprising at least two liquid-crystalline components, wherein at least one component is a fluorobenzene compound of the formula I,

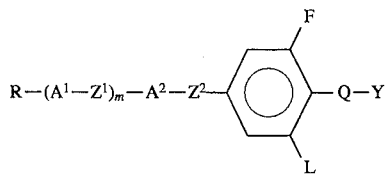

in which

R is H or allyl or 1 to 15 carbon atoms which is unsubstituted or monosubstituted by CN or CF$_3$ and in which one or more CH$_2$ groups can be replaced, in each case independently of one another, by

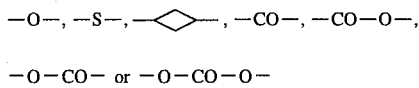

—O—CO— or —O—CO—O— in such a manner that O atoms are not linked directly to one another,

A$^1$ and A$^2$, in each case independently of one another, are a (a) trans-1,4-cyclohexylene in which one or more non-adjacent CH$_2$ groups can also be replaced by —O— and/or —S—, (b) 1,4-phenylene in which one or two CH groups can also be replaced by N, (c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, wherein only one of A$^1$ and A$^2$ is Phe in which Phe is 1,4-phenylene which is unsubstituted or mono- or disubstituted by F or Cn, it being possible for the radicals (a) and (b) to be substituted by CN or fluorine, Z$^1$ and Z$^2$, in each case independently of one another, are —CO—O—, —O—CO—, —CH$_2$O—, —OCH$_2$—, —CH$_2$CH$_2$—, —CH=CH—, —C≡C— or a single bond, one of Z$^1$ and Z$^2$ can also be —(CH$_2$)$_4$— or —CH=CH—CH$_2$CH$_2$—, L is F, m is 0, 1 or 2, Y is F or Cl, and Q is a single bond; and wherein said medium contains 45–90 wt. % of compounds of formula I.

2. A liquid-crystal display element containing a liquid-crystalline medium, the improvement wherein said medium is a medium according to claim 1.

3. In an electrooptical display element containing a dielectric, the improvement wherein said dielectric is a liquid-crystalline medium according to claim 1.

4. A liquid-crystalline medium according to claim 1, wherein R is alkyl of 1–15 C atoms, n is 0, A$^2$ is trans-1,4-cyclohexylene, Z$^2$ is a single bond and Y is F.

5. A liquid-crystalline medium according to claim 4, wherein R is alkyl of 2–7 C atoms.

6. A liquid-crystalline medium according to claim 1, wherein R is alkyl of 1–15 C atoms, m is 0, A$^2$ is trans-1,4-cyclohexylene, Z$^2$ is —CH$_2$CH$_2$— and Y is F.

7. A liquid-crystalline medium according to claim 6, wherein R is alkyl of 2–7 C atoms.

8. A liquid-crystalline medium according to claim 1, wherein R is alkyl of 1–15 C atoms, m is 1, A$^1$ is trans-1,4-cyclohexylene, Z$^1$ is a single bond, A$^2$ is 1,4-phenylene, Z$^2$ is a single bond, and Y is F.

9. A liquid-crystalline medium according to claim 1, wherein R is alkyl of 1–15 C atoms, m is 1, A$^1$ is trans-1,4-cyclohexylene, Z$^1$ is —CH$_2$CH$_2$—, A$^2$ is 1,4-phenylene, Z$^2$ is a single bond, and Y is F.

10. A liquid-crystalline medium according to claim 1, wherein Z$^1$ is —O—CO—, —CH$_2$O—, —OCH$_2$—, —CH$_2$CH$_2$—, —CH=CH—, —C≡C—, a single bond, —(CH$_2$)$_4$—, or —CH=CH—CH$_2$CH$_2$—.

11. A liquid-crystalline medium according to claim 1, wherein m is 0 or 1.

12. A liquid-crystalline medium according to claim 1, wherein said medium contains at least one compound of the formula

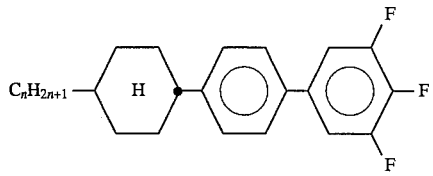

wherein n is 1–15.

13. A liquid crystal medium according to claim 12, wherein said mixture contains at least 8 wt % of said compound.

14. A liquid crystal medium according to claim 12, wherein said mixture contains at least 24 wt % of said compound.

15. A fluorobenzene compound according to claim 1, wherein said compound is of formula I'

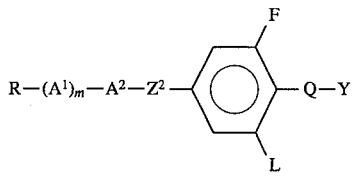

wherein

R is H, an alkyl or alkenyl radical of 1–15 C atoms which is unsubstituted or monosubstituted by CN, $CF_3$, or halogen it being possible for one or more $CH_2$ groups in each radicals also be replaced, in each case independently of one another, by

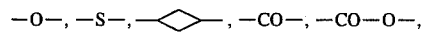

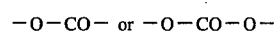

in such a manner that O atoms are not linked directly to one another;

$A^1$ and $A^2$, in each case independently of one another, are a
(a) trans-1,4-cyclohexylene radical, in which one or more non-adjacent $CH_2$ groups can also be replaced by —O— and/or —S—,
(b) 1,4-phenylene radical, in which one or two CH groups can also be replaced by N,
(c) radical from the group comprising 1,4-cyclohexenylene, 1,4-bicyclo(2.2.2)octylene, piperidine-1,4-diyl, naphthalene-2,6-diyl, decahydronaphthalene-2,6-diyl and 1,2,3,4-tetrahydronaphthalene- 2,6-diyl, it being possible for the radicals (a) and (b) to be substituted by CN or fluorine, m is 0, 1, or 2;

L is F;

Y is F or Cl;

Q is a single bond; and $Z^2$ is —$(CH_2)_4$— or —CH=CH—$CH_2CH_2$—.

16. A fluorobenzene compound of formula Ii

R—$A^1$—$A^1$—$Z^1$—$A^2$—$A^3$—Q—Y      Ii,

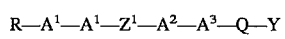

wherein

R is H or alkyl of 1 to 15 carbon atoms which is unsubstituted or monosubstituted by CN, $CF_3$ or halogen and in which one or more $CH_2$ groups can be replaced, in each case independently of one another, by

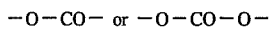

in such a manner that O atoms are not linked directly to one another;

$A^1$ and $A^2$, in each case independently of one another, are a
(a) trans-1,4-cyclohexylene in which one or more non-adjacent $CH_2$ groups can also be replaced by —O— and/or —S—,
(b) 1,4-phenylene in which one or two CH groups can also be replaced by N,
(c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radicals (a) and (b) to be substituted by CN or fluorine, wherein only one of $A^1$ and $A^2$ is Phe in which Phe is 1,4-phenylene which is unsubstituted or mono- or disubstituted by F or CN:

$A^3$ is

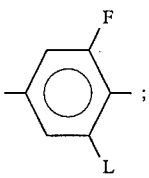

$Z^1$ is —CO—O—, —O—CO—, —$CH_2$O—, —O$CH_2$—, —$CH_2CH_2$—, —CH=CH—, —C≡C—, a single bond, —$(CH_2)_4$— or —CH=CH—$CH_2CH_2$—;

L is F;

Y is F or Cl; and

Q is a single bond.

17. A fluorobenzene compound of formula II

R—$A^1$—$A^1$—$Z^1$—$A^2$—$Z^2$—$A^3$—Q—Y      II, wherein

R is H or alkyl of 1 to 15 carbon atoms which is unsubstituted or monosubstituted by CN, $CF_3$ or halogen and in which one or more $CH_2$ groups can be replaced, in each case independently of one another, by

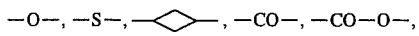

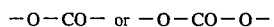

in such a manner that O atoms are not linked directly to one another;

$A^1$ and $A^2$, in each case independently of one another, are a
(a) trans-1,4-cyclohexylene in which one or more non-adjacent $CH_2$ groups can also be replaced by —O— and/or —S—,
(b) 1,4-phenylene in which one or two CH groups can also be replaced by N,
(c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radicals (a) and (b) to be substituted by CN or fluorine,
wherein only one of $A^1$ and $A^2$ is Phe in which Phe is 1,4-phenylene which is unsubstituted or mono- or disubstituted by F or CN;

$A^3$ is

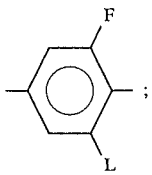;

$Z^1$ and $Z^2$, in each case independently of one another, are —CO—O—, —O—CO—, —CH$_2$O—, —OCH$_2$—, —CH$_2$CH$_2$—, —CH=CH—; —C≡C— or a single bond, one of the radicals $Z^1$ and $Z^2$ can also be —(CH$_2$)$_4$— or —CH=CH—CH$_2$CH$_2$—, L is F;

Y is F or Cl; and

Q is a single bond.

18. A fluorobenzene compound of the formula I,

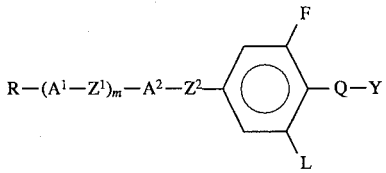

wherein

R is H or alkyl of 1 to 15 carbon atoms which is unsubstituted or monosubstituted by CN or CF$_3$ and in which one or more CH$_2$ groups can be replaced, in each case independently of one another, by

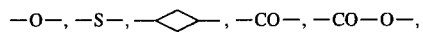

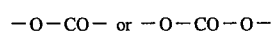

in such a manner that O atoms are not linked directly to one another;

$A^1$ and $A^2$, in each case independently of one another, are a (a) trans-1,4-cyclohexylene in which one or more non-adjacent CH$_2$ groups can also be replaced by —O— and/or —S—, (b) 1,4-phenylene in which one or two CH groups can also be replaced by N, (c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radicals (a) and (b) to be substituted by CN or fluorine, wherein at least one of $A^1$ and $A^2$ is 2-fluoro-1,4-phenylene, 3-fluoro-1,4-phenylene, or 3,5-difluoro-1,4-phenylene, and wherein only one of $A^1$ and $A^2$ is Phe in which Phe is 1,4-phenylene which is unsubstituted or mono- or disubstituted by F or CN;

$Z^1$ and $Z^2$, in each case independently of one another, are —CO—O—, —O—CO—, —CH$_2$O—, —OCH$_2$—, —CH$_2$Ch$_2$—, —CH=CH—, —C≡C— or a single bond, one of the radicals $Z^1$ and $Z^2$ can also be —(CH$_2$)$_4$— or —CH=CH—CH$_2$CH$_2$—;

L is F;

m is 0, 1 or 2;

Y is F or Cl; and

Q is a single bond.

19. A fluorobenzene compound according to claim 18, wherein $A^2$ is 3,5-difluoro-1,4-phenylene, and m is 1 or 2.

20. A fluorobenzene compound of the formula I,

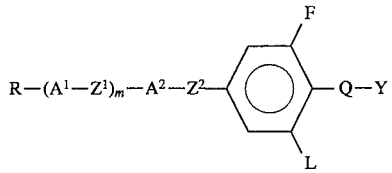

wherein

R is straight-chain oxaalkyl or 2–9 C atoms, $A^1$ and $A^2$, in each case independently of one another, are a (a) trans-1,4-cyclohexylene in which one or more non-adjacent CH$_2$ groups can also be replaced by —O— and/or —S—, (b) 1,4-phenylene in which one or two CH groups can also be replaced by N, (c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radicals (a) and (b) to be substituted by CN or fluorine, wherein only one of $A^1$ and $A^2$ is Phe in which Phe is 1,4-phenylene which is unsubstituted or mono- or disubstituted by F or CN;

$Z^1$ and $Z^2$, in each case independently of one another, are —CO—O—, —O—CO—, —CH$_2$O—, —OCH$_2$—, —CH$_2$Ch$_2$—, —CH=CH—, —C≡C— or a single bond, one of the radicals $Z^1$ and $Z^2$ can also be —(CH$_2$)$_4$— or —Ch=CH—CH$_2$CH$_2$—;

L is F;

m is 0, 1 or 2;

Y is F or Cl; and

Q is a single bond.

21. A fluorobenzene compound of the formula I,

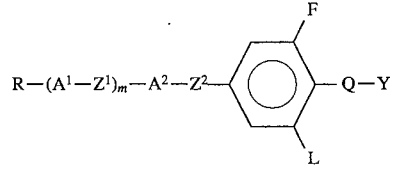

wherein

R is H or alkyl of 1 to 15 carbon atoms which is unsubstituted or monosubstituted by CN, CF$_3$ or halogen and in which one or more CH$_2$ groups can be replaced, in each case independently of one another, by

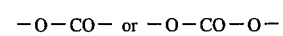

in such a manner that O atoms are not linked directly to one another;

$A^1$ and $A^2$, in each case independently of one another, are a (a) trans-1,4-cyclohexylene in which one or more nonadjacent $CH_2$ groups can also be replaced by —O— and/or —S—,
(b) 1,4-phenylene in which one or two CH groups can also be replaced by N,
(c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radicals (a) and (b) to be substituted by CN or fluorine;

$Z^1$ and $Z^2$, in each case independently of one another, are —CO—O—, —O—CO—, —$CH_2$O—, —O$CH_2$—, —$CH_2CH_2$—, —CH=CH—, —C≡C— or a single bond, one of the radicals $Z^1$ and $Z^2$ can also be —$(CH_2)_4$— or —CH=CH—$CH_2CH_2$—, and at least one of $Z^1$ and $Z^2$ is —C≡C—;

L is F;

m is 0, 1 or 2;

Y is F or Cl; and

Q is a single bond.

22. A liquid-crystalline medium comprising at least two liquid-crystalline components, wherein at least one component is a fluorobenzene compound of the formula I,

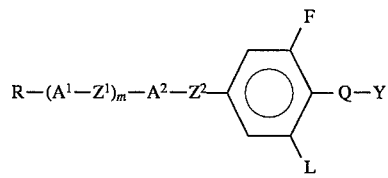

in which

R is H or alkyl of 1 to 15 carbon atoms which is unsubstituted or monosubstituted by CN or $CF_3$ and in which one or more $CH_2$ groups can be replaced, in each case, independently of one another, by

—O—, —S—, —◇—, —CO—, —CO—O—,

—O—CO— or —O—CO—O— in such a manner that O atoms are not linked directly to one another, $A^1$ and $A^2$, in each case independently of one another, are a
(a) trans-1,4-cyclohexylene in which one or more nonadjacent $CH_2$ groups can also be replaced by —O— and/or —S—,
(b) 1,4-phenylene in which one or two CH groups can also be replaced by N,
(c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl it being possible for the radicals (a) and (b) to be substituted by CN or fluorine, wherein at least one of $A^1$ and $A^2$ is trans-1,4-cyclohexylene in which one or more nonadjacent $CH_2$ groups can also be replaced by —O— and/or —S—, $Z^1$ and $Z^2$, in each case independently of one another, are —CO—O—, —O—CO—, —$CH_2$O—, —O$CH_2$—, —$CH_2C_2$—, —CH=CH—, —C≡C— or a single bond, one of $Z^1$ and $Z^2$ can also be —$(CH_2)_4$— or —CH=CH—$CH_2CH_2$—, L is F, m is 0, 1 or 2, Y is F or Cl, and Q is a single bond; and wherein said medium contains 45–90 wt. % of compounds of formula I.

23. A liquid-crystalline medium according to claim 22, wherein Y is F.

24. A liquid-crystalline medium according to claim 23, wherein R is alkyl of 1–15 C atoms, m is 1, $A^1$ is trans-1,4-cyclohexylene, $Z^1$ is a single bond, $A^2$ is trans-1,4-cyclohexylene, $Z^2$ is a single bond, and Y is F.

25. A liquid-crystalline medium according to claim 23, wherein R is alkyl of 1–15 C atoms, m is 1, $A^1$ is trans-1,4-cyclohexylene, $Z^1$ is —$CH_2CH_2$—, $A^2$ is trans-1,4-cyclohexylene, $Z^2$ is a single bond, and Y is F.

26. A liquid-crystalline medium according to claim 23, wherein R is alkyl of 1–15 C atoms, m is 1, $A^1$ is trans-1,4-cyclohexylene, $Z^1$ is a single bond, $A^2$ is trans-1,4-cyclohexylene, $Z^2$ is —$CH_2CH_2$—, and Y is F.

27. A liquid-crystalline medium according to claim 23, wherein R is alkyl of 1–15 C atoms, m is 1, $A^1$ is trans-1,4-cyclohexylene, $Z^1$ is —$CH_2CH_2$—, $A^2$ is trans-1,4-cyclohexylene, $Z^2$ is —$CH_2CH_2$—, and Y is F.

28. A liquid-crystalline medium comprising at least two liquid-crystalline components, wherein at least one component is a fluorobenzene compound of the formula I,

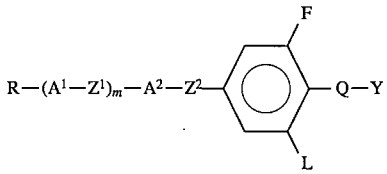

in which

R is H or alkyl of 1 to 15 carbon atoms which is unsubstituted or monosubstituted by CN or $CF_3$ and in which one or more $CH_2$ groups can be replaced, in each case independently of one another, by

—O—, —S—, —◇—, —CO—, —CO—O—,

—O—CO— or —O—CO—O— in such a manner that O atoms are not linked directly to one another, $A^1$ and $A^2$, in each case independently of one another, are a
(a) trans-1,4-cyclohexylene in which one or more nonadjacent $CH_2$ groups can also be replaced by —O— and/or —S—,
(b) 1,4-phenylene in which one or two CH groups can also be replaced by N,
(c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radicals (a) and (b) to be substituted by CN or fluorine.

$Z^1$ and $Z^2$, in each case independently of one another, are —CO—O—, —O—CO—, —$CH_2$O—, —O$CH_2$—, —CH=CH—, —C≡C— or a single bond, one of $Z^1$ and $Z^2$ can also be —$(CH_2)_4$— or —CH=CH—$CH_2CH_2$—, L is F, m is 0, 1 or 2, Y is F or Cl, and Q is a single bond; and wherein said medium contains 45–90 wt. % of compounds of formula I.

29. A liquid-crystalline medium according to claim 28, wherein $Z^1$ is —O—CO—, —CH$_2$O—, —OCH$_2$—, —CH=CH—, —C≡C—, a single bond, —(CH$_2$)$_4$—, or —CH=CH—CH$_2$CH$_2$—.

30. A liquid-crystalline medium according to claim 28, wherein m is 0 or 1.

31. A fluorobenzene compound of formula Ii

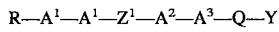    Ii, wherein

R is H or alkyl of 1 to 15 carbon atoms which is unsubstituted or monosubstituted by CN, CF$_3$ or halogen and in which one or more CH$_2$ groups can be replaced, in each case independently of one another, by

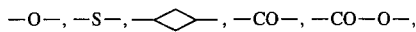

in such a manner that O atoms are not linked directly to one another;

$A^1$ and $A^2$, in each case independently of one another, are a (a) trans-1,4-cyclohexylene in which one or more non-adjacent CH$_2$ groups can also be replaced by —O— and/or —S—, (b) 1,4-phenylene in which one or two CH groups can also be replaced by N, (c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radicals (a) and (b) to be substituted by CN or fluorine;

$A^3$ is

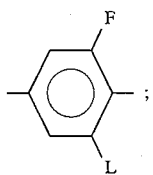

$Z^1$ is —CO—O—, —O—CO—, —CH$_2$O—, —OCH$_2$13 , —CH=CH—, —C≡C—, a single bond, —(CH$_2$)$_4$— or —CH=CH—CH$_2$CH$_2$—;

L is F;

Y is F or Cl; and

Q is a single bond.

32. A fluorobenzene compound of formula I1

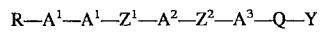    I1, wherein

R is H or alkyl of 1 to 15 carbon atoms which is unsubstituted or monosubstituted by CN, CF$_3$ or halogen and in which one or more CH$_2$ groups can be replaced, in each case independently of one another, by

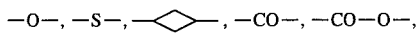

in such a manner that O atoms are not linked directly to one another;

$A^1$ and $A^2$, in each case independently of one another, are a (a) trans-1,4-cyclohexylene in which one or more non-adjacent CH$_2$ groups can also be replaced by —O— and/or —S—, (b) 1,4-phenylene in which one or two CH groups can also be replaced by N, (c) 1,4-cyclohexenylene, 1,4-bicyclo(2.2.2)octylene, piperidine-1,4-diyl, naphthalene-2,6-diyl, decahydronaphthalene-2,6-diyl or 1,2,3,4-tetrahydronaphthalene- 2,6-diyl, it being possible for the radical (a) and (b) to be substituted by CN or fluorine;

$A^3$ is

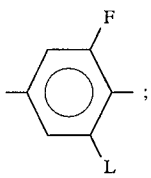

$Z^1$ and $Z^2$, in each case independently of one another, are —CO—O—, —O—CO—, —CH$_2$O—, —OCH$_2$—, —CH=CH—; —C≡C— or a single bond, one of the radicals $Z^1$ and $Z^2$ can also be —(CH$_2$)$_4$— or —CH=CH—CH$_2$CH$_2$—, L is F;

Y is F or Cl; and

Q is a single bond.

33. A fluorobenzene compound of the formula I,

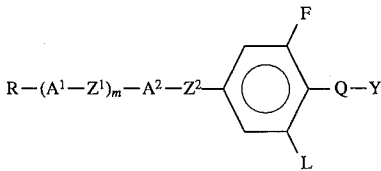

wherein

R is H or alkyl of 1 to 15 carbon atoms which is unsubstituted or monosubstituted by CN or CF$_3$ and in which one or more CH$_2$ groups can be replaced, in each case independently of one another, by

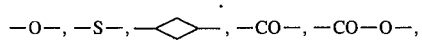

in such a manner that O atoms are not linked directly to one another;

$A^1$ and $A^2$, in each case independently of one another, are a (a) trans-1,4-cyclohexylene in which one or more non-adjacent CH$_2$ groups can also be replaced by —O— and/or —S—, (b) 1,4-phenylene in which one or two CH groups can also be replaced by N, (c) 1,4-cyclohexenylene, 1,4-bicyclo(2.2.2)octylene, piperidine-1,4-diyl, napthalene-2,6-diyl, decahydronaphthalene-2,6-diyl or 1,2,3,4-tetrahydronaphthalene- 2,6-diyl, it being possible for the radicals (a) and (b) to be substituted by CN or fluorine, wherein at least one of $A^1$ and $A^2$ is 2-fluoro-1,4-phenylene, 3-fluoro-1,4-phenylene, or 3,5-difluoro-1,4-phenylene;

$Z^1$ and $Z^2$, in each case independently of one another, are —CO—O—, —O—CO—, —CH$_2$O—, —OCH$_2$—, —CH=CH—, —C≡C— or a single bond, one of the radicals $Z^1$ and $Z^2$ can also be —(CH$_2$)$_4$— or —CH=CH—CH$_2$CH$_2$—;

L is F;

m is 0, 1 or 2;

Y is F or Cl; and

Q is a single bond.

34. A fluorobenzene compound according to claim 52, wherein said compound is of formula Ife R—Phe—Phe—A³—Q—Y wherein R is H or alkyl of 1 to 15 carbon atoms which is unsubstituted or monosubstituted by CN or CF$_3$ and in which one or more CH$_2$ groups can be replaced, in each case independently of one another, by —O—, —S—, , —CO—, —CO—O—, —O—CO— or —O—CO—O— in such a manner that O atoms are not linked directly to one another;

Phe is 1,4-phenylene which is unsubstituted or mono- or disubstituted by F or CN;

A³ is

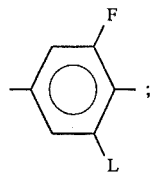

A is a single bond;

L is F; and

Y is F or Cl.

35. A fluorobenzene compound according to claim 34, wherein said compound is 4"-n-propyl-2",3,4,5-tetrafluoroterphenyl or 4"-n-pentyl- 2",3,4,5-tetrafluoroterphenyl.

36. A fluorobenzene compound of the formula I,

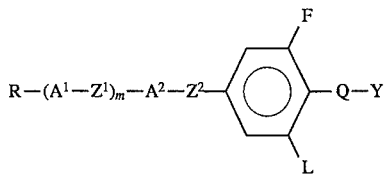

wherein

R is straight-chain oxaalkyl of 2–9 C atoms, $A^1$ and $A^2$, in each case independently of one another, are a
(a) trans-1,4-cyclohexylene in which one or more non-adjacent CH$_2$ groups can also be replaced by —O— and/or —S—, 1,4-phenylene in which one or two CH groups can also be replaced by N, (c) 1,4-cyclohexenylene, 1,4-bicyclo(2.2.2)octylene, piperidine-1,4-diyl, naphthalene-2,6-diyl, decahydronaphthalene-2,6idyl or 1,2,3,4-tetrahydronaphthalene- 2,6-diyl, it being possible for the radicals (a) and (b) to be substituted by CN or fluorine;

$Z^1$ and $Z^2$, in each case independently of one another, are —CO—O—, —O—CO—, —CH$_2$O—, —OCH$_2$—, —CH=CH—, —C≡C— or a single bond, one of the radicals $Z^1$ and $Z^2$ can also be —(CH$_2$)$_4$— or —CH=CH—CH$_2$CH$_2$—;

L is F;

m is 0, 1 or 2;

Y is F or Cl, and

Q is a single bond.

* * * * *

UNITED STATES PATENT AND TRADEMARK OFFICE
CERTIFICATE OF CORRECTION

PATENT NO. : 5,487,845
DATED : January 30, 1996
INVENTOR(S) : Volker REIFFENRATH et al, It is certified that error appears in the above-indentified patent and that said Letters Patent is hereby corrected as shown below:

Claim 33; column 69, line 5:

Change " $A^1$ and $A^2$ " to read -- $A^1$ and $A^2$ --.

Claim 34; column 69, line 16:

Change "claim 52" to read -- claim 33 --.

Signed and Sealed this

Eighteenth Day of February, 1997

Attest:

BRUCE LEHMAN

Attesting Officer     Commissioner of Patents and Trademarks